US010058347B2

(12) United States Patent
Hirai et al.

(10) Patent No.: US 10,058,347 B2
(45) Date of Patent: Aug. 28, 2018

(54) HANDLE UNIT AND SURGICAL DEVICE

(71) Applicant: OLYMPUS CORPORATION, Tokyo (JP)

(72) Inventors: Yuji Hirai, Ebina (JP); Eiji Murakami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 367 days.

(21) Appl. No.: 14/729,849

(22) Filed: Jun. 3, 2015

(65) Prior Publication Data

US 2015/0335347 A1    Nov. 26, 2015

Related U.S. Application Data

(63) Continuation of application No. PCT/JP2014/064020, filed on May 27, 2014.

(30) Foreign Application Priority Data

Jun. 6, 2013  (JP) .................... 2013-119903

(51) Int. Cl.
  *A61B 17/32*  (2006.01)
  *A61N 7/00*   (2006.01)
  (Continued)

(52) U.S. Cl.
  CPC ........ *A61B 17/320092* (2013.01); *A61N 7/00* (2013.01); *A61B 18/1445* (2013.01);
  (Continued)

(58) Field of Classification Search
  CPC .... A61B 18/1445; A61B 2017/320096; A61B 17/320092
  See application file for complete search history.

(56) References Cited

U.S. PATENT DOCUMENTS 6,039,752 A     3/2000  Kimura et al.
7,846,177 B2 * 12/2010  Carpenter .......... A61B 17/2909
                                              606/205
2007/0299469 A1 12/2007  Carpenter et al.

FOREIGN PATENT DOCUMENTS

CN    101534729 A    9/2009
DE      4428479 A1   2/1996
(Continued)

OTHER PUBLICATIONS

Dec. 8, 2015 International Preliminary Report on Patentability issued in International Patent Application No. PCT/JP2014/064020.
(Continued)

*Primary Examiner* — Kathleen Holwerda
*Assistant Examiner* — Christina Lauer
(74) *Attorney, Agent, or Firm* — Oliff PLC

(57) ABSTRACT

A handle unit for a surgical device that operates an end effector to give various kinds of treatments, includes: a handle main body having a fixed member; a support section that is supported by the same hand of the user and is movable along a turning plane defined by moving closer to or away from the fixed member; a first coupling section that is coupled with the handle main body by moving the support section along the turning plane; a second coupling section that has an extended axis defined by the first coupling section and the support section and is configured to turn the support section in a periaxial direction orthogonal to the extended axis; and a third coupling section that is configured to turn the support section in the periaxial direction of the extended axis.

15 Claims, 24 Drawing Sheets

(51) Int. Cl.
  *A61B 18/14*    (2006.01)
  *A61B 18/00*    (2006.01)
  *A61B 17/00*    (2006.01)
  *A61B 17/29*    (2006.01)

(52) U.S. Cl.
  CPC ............... *A61B 2017/00424* (2013.01); *A61B 2017/291* (2013.01); *A61B 2017/2911* (2013.01); *A61B 2017/2929* (2013.01); *A61B 2018/00994* (2013.01)

(56) References Cited

FOREIGN PATENT DOCUMENTS

| DE | 202008004539 U1 | 6/2008 |
|----|-----------------|--------|
| JP | 2003135474 A | 5/2003 |
| JP | 2006-068537 A | 3/2006 |
| JP | 2009541013 A | 11/2009 |
| NL | 1012856 C2 | 2/2001 |
| WO | 2005112795 A1 | 12/2005 |
| WO | 2009046234 A2 | 4/2009 |

OTHER PUBLICATIONS

Nov. 1, 2016 Office Action issued in Japanese Patent Application No. 2015-516371.
Jan. 31, 2017 Extended Search Report issued in European Patent Application No. 14806980.0.
Aug. 4, 2015 Office Action issued in Japanese Patent Application No. 2015-516371.
Jul. 8, 2014 International Search Report issued in International Application No. PCT/JP2014/064020.
Nov. 17, 2015 Office Action issued in Japanese Patent Application No. 2015-516371.
Jun. 1, 2017 Office Action issued in Chinese Patent Application No. 201480044745.6.

* cited by examiner

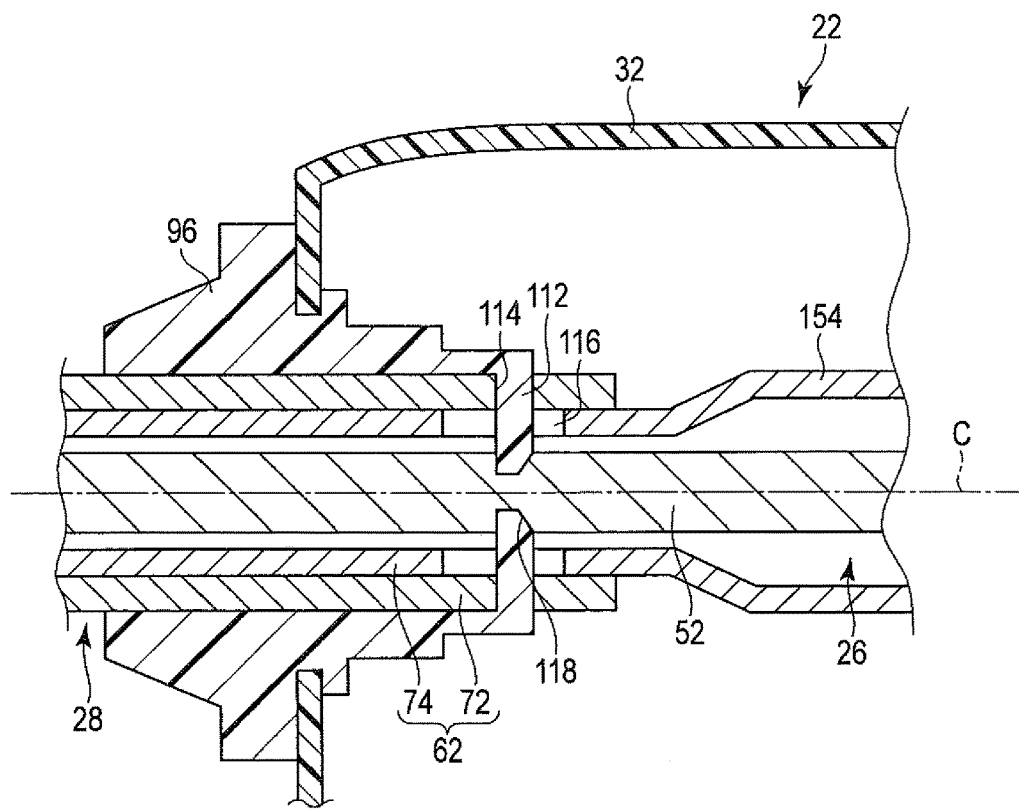
F I G. 5
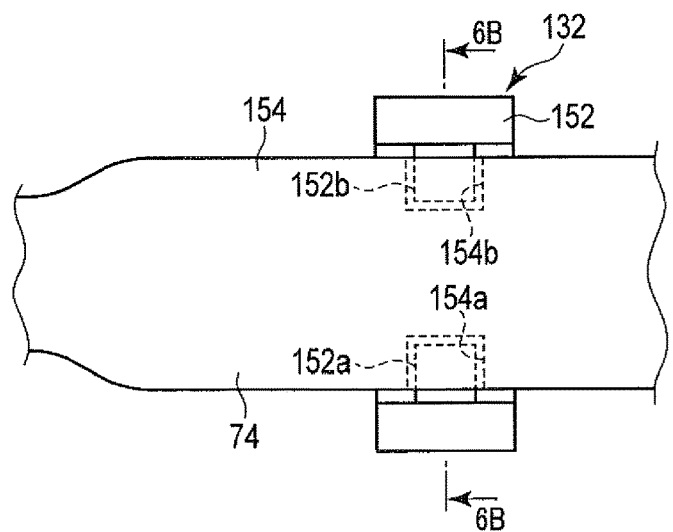
F I G. 6A

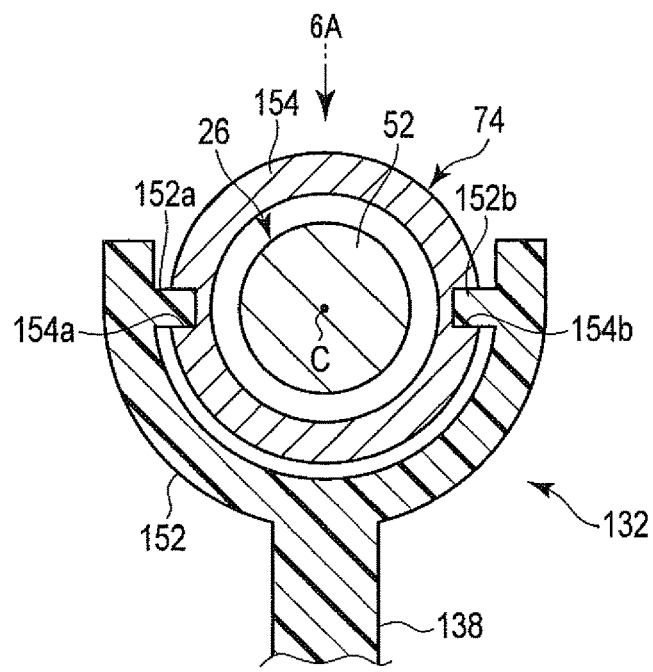
F I G. 6B
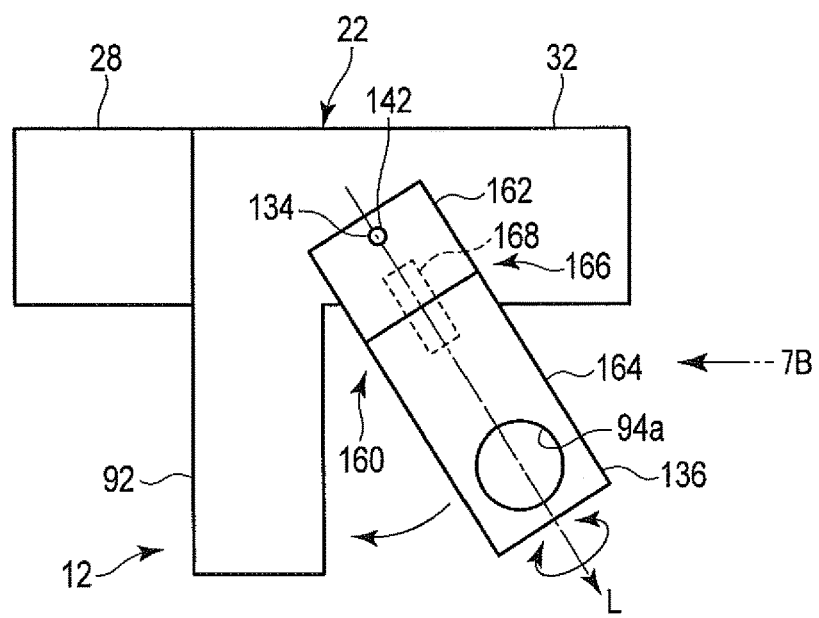
F I G. 7A

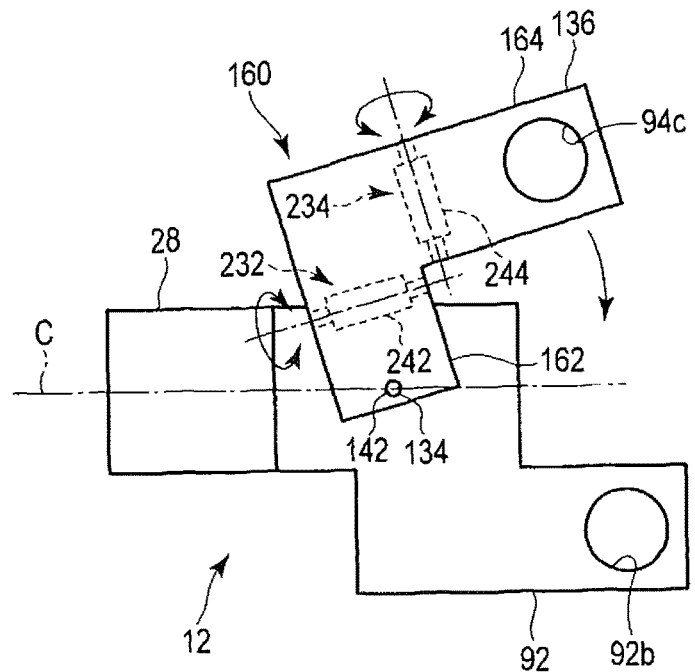
F I G. 14
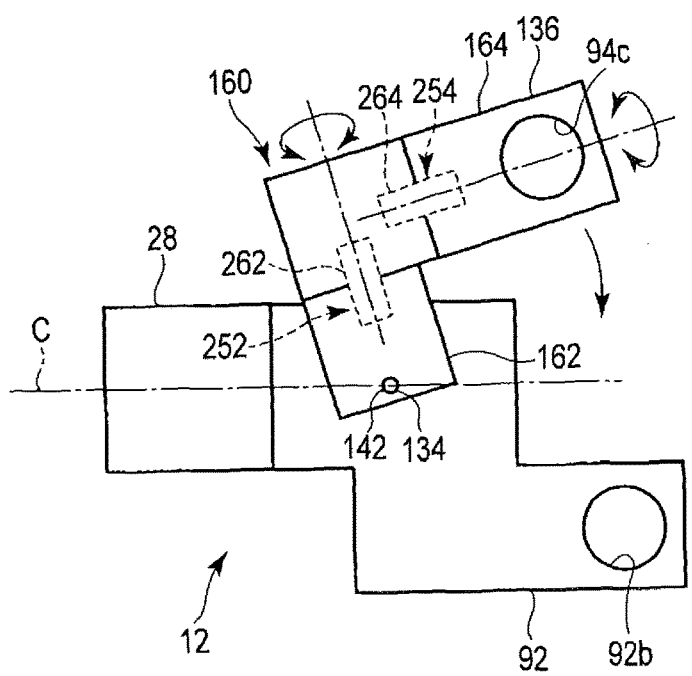
F I G. 15

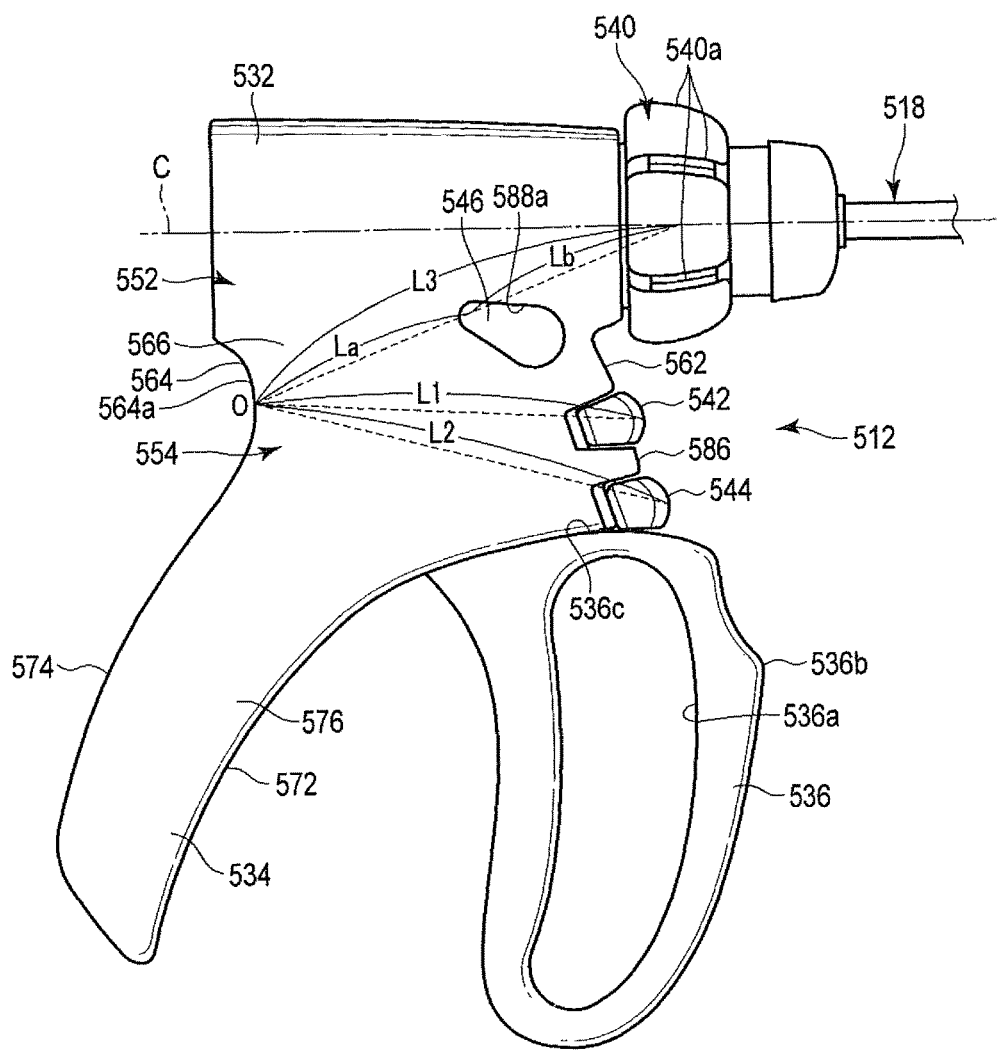
F I G. 20

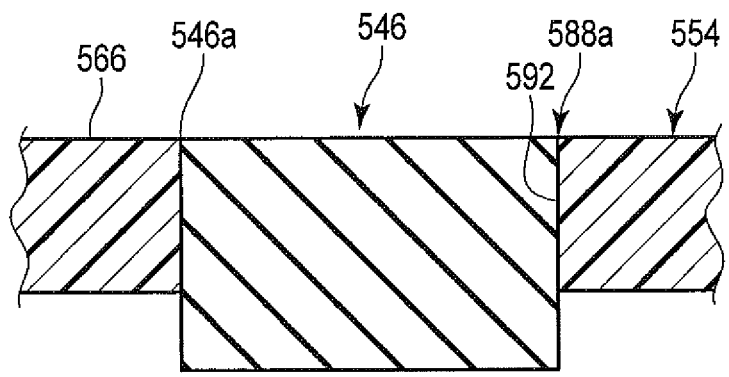
F I G. 21A
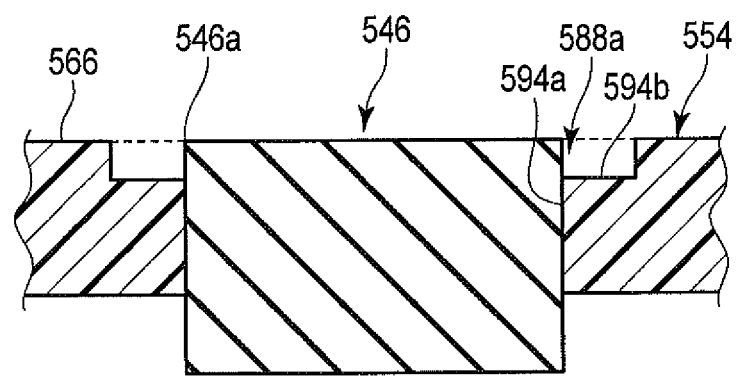
F I G. 21B

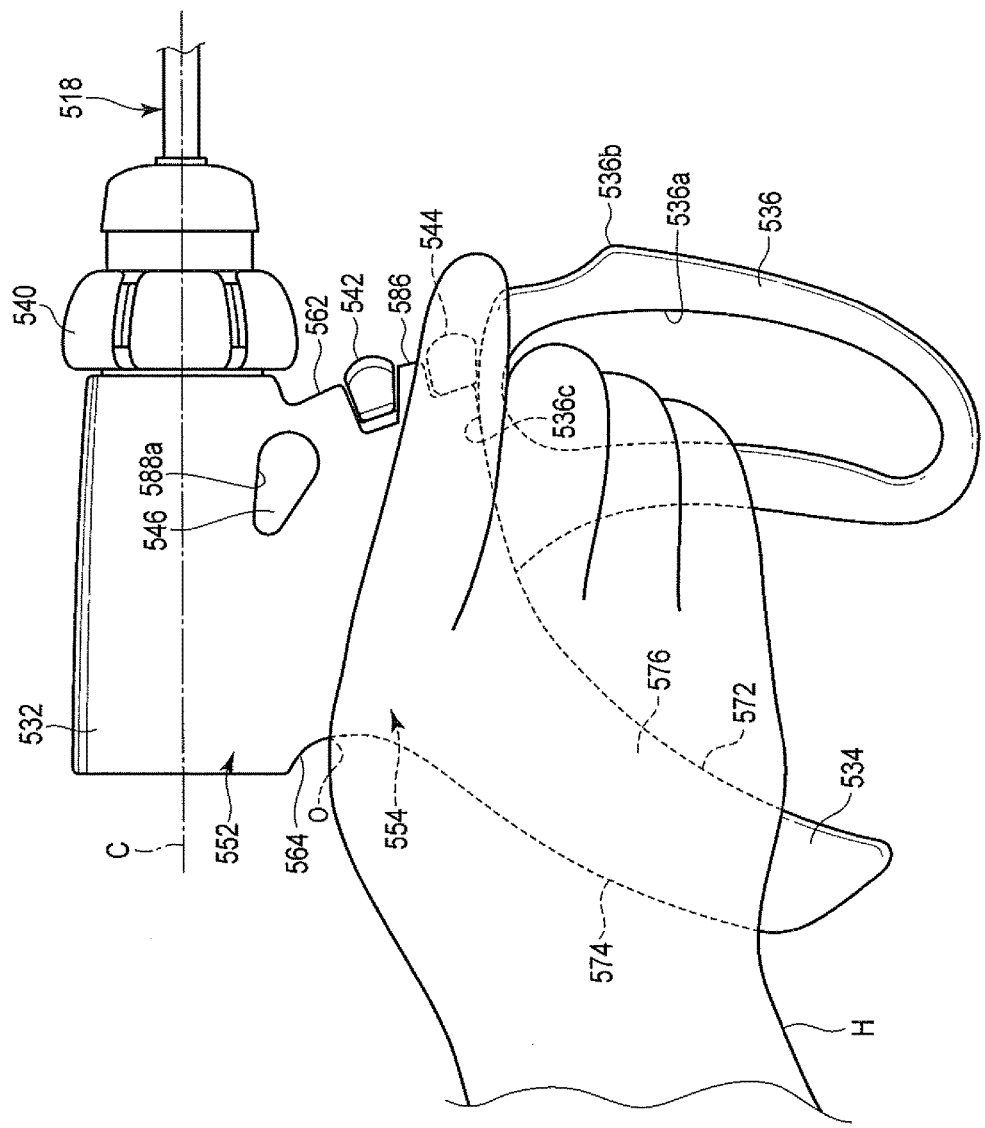
F I G. 22A

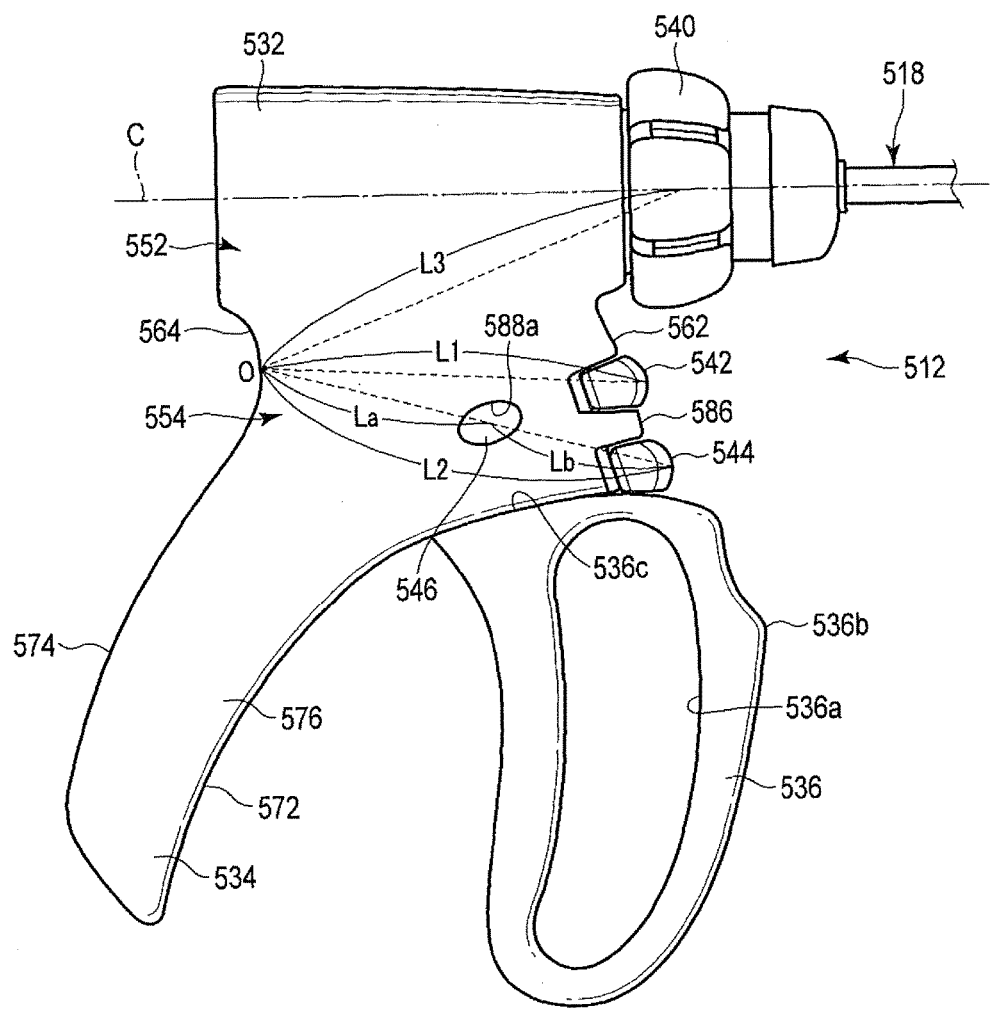
F I G. 23

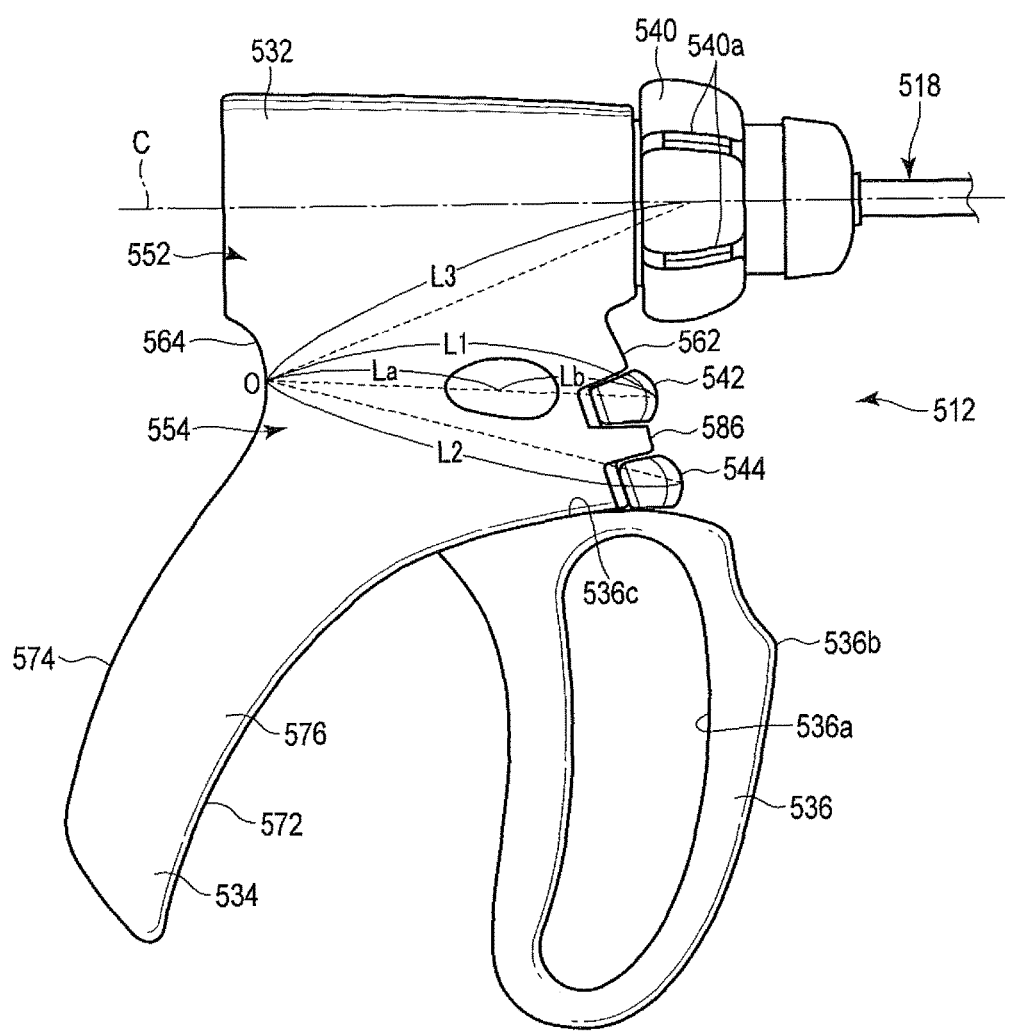
F I G. 24

US 10,058,347 B2

HANDLE UNIT AND SURGICAL DEVICE

CROSS-REFERENCE TO RELATED APPLICATIONS

This application is a Continuation Application of PCT Application No. PCT/JP2014/064020, filed May 27, 2014 and based upon and claiming the benefit of priority from prior Japanese Patent Application No. 2013-119903, filed Jun. 6, 2013, the entire contents of all of which are incorporated herein by reference.

BACKGROUND OF THE INVENTION

1. Field of the Invention

The present invention relates to a handle unit of a surgical device and the surgical device.

2. Description of the Related Art

For example, International Publication No. WO 2005/112795 discloses a surgical device. In this device, a jaw can be opened or closed by moving a movable handle (a moving member) to a fixed handle (a fixed member). Further, in this device, a direction of the fixed handle can be adjusted to the movable handle.

BRIEF SUMMARY OF THE INVENTION

According to one aspect of the present invention, there is provided a handle unit for a surgical device that operates an end effector to give various kinds of treatments, includes: a handle main body having a fixed member; a support section that is supported by the same hand of the user to maintain a position of the end effector in a positioned state and is movable along a turning plane defined by moving closer to or away from the fixed member; a first coupling section that is coupled with the handle main body by moving the support section along the turning plane; a second coupling section that has an extended axis defined by the first coupling section and the support section and is configured to turn the support section in a periaxial direction orthogonal to the extended axis; and a third coupling section that is configured to turn the support section in the periaxial direction of the extended axis.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a longitudinal sectional view showing a configuration of a coupling section of a sheath unit, a handle unit, and the probe in the surgical device according to the first to third embodiments;

FIG. 6A is a schematic plan view showing a coupling configuration of a movable handle and a drive pipe in the surgical device according to the first to third embodiments;

FIG. 6B is a schematic transverse sectional view taken along a line 6B-6B in FIG. 6A;

FIG. 7A is a schematic side view showing a configuration of the movable handle that is openable/closable to a fixed handle in the handle unit of the surgical device according to the first embodiment;

FIG. 14 is a schematic side view showing a configuration of a movable handle that is openable/closable to a fixed handle in a handle unit of the surgical device according to the fifth embodiment;

FIG. 15 is a schematic side view showing a configuration of a movable handle that is openable/closable to a fixed handle in a handle unit of a surgical device according to a sixth embodiment;

FIG. 20 is a schematic side view showing a right side surface of the handle unit in the surgical system according to the first reference embodiment;

FIG. 21A is a schematic cross-sectional view showing a state that a third switch is arranged on the right side surface of the handle unit in the surgical system according to the first reference embodiment;

FIG. 21B is a schematic cross-sectional view showing a state that the third switch is arranged on the right side surface of the handle unit in the surgical system according to the first reference embodiment which is modified to FIG. 21A;

FIG. 22A is a schematic right side view showing a state that a finger sphere of a fingertip of an index finger is arranged on a second switch while holding the handle unit of the surgical system according to the first reference embodiment by a right hand;

FIG. 23 is a schematic side view showing a right side surface of a handle unit of a surgical system according to a second reference embodiment;

FIG. 24 is a schematic side view showing a right side surface of a handle unit of a surgical system according to a third reference embodiment.

DETAILED DESCRIPTION OF THE INVENTION

Modes for embodying the present invention will now be described hereinafter with reference to the drawings.

A first embodiment will be described with reference to FIG. 1 to FIG. 8B.

Figure 1:
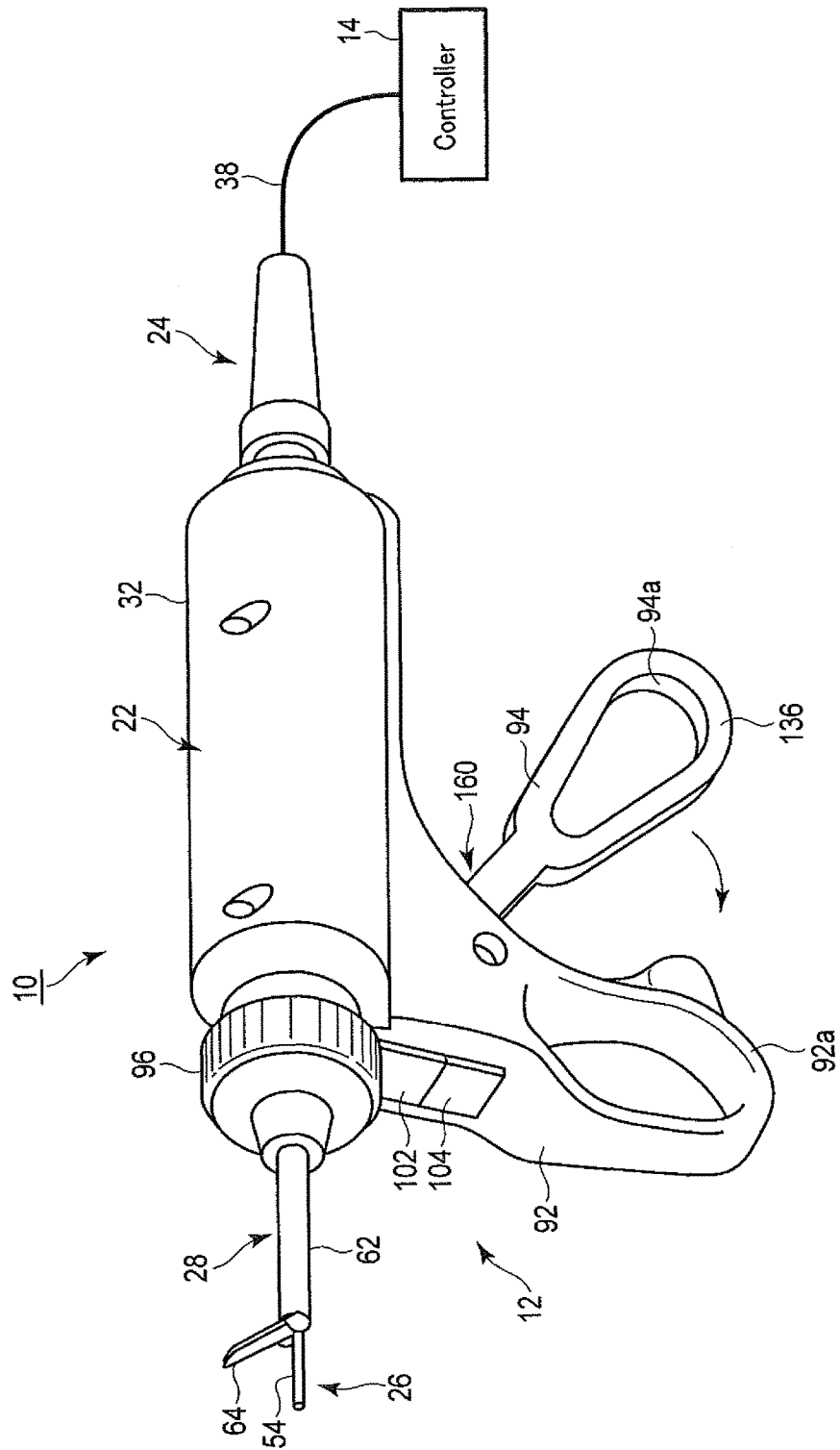
FIG. 1 is a schematic view showing a surgical system according to first to third embodiments.

As shown in FIG. 1, a surgical system 10 according to this embodiment includes a surgical device 12 and a controller 14 that controls the device 12. It is to be noted that, in this embodiment and later-described second to sixth embodiments, a description will be given on the assumption that the surgical device 12 is an ultrasonic treatment tool.

The surgical device 12 includes a handle unit 22, an ultrasonic transducer unit 24, a probe 26, and a sheath unit 28 that operate a later-described end effector to give various kinds of treatments. The handle unit 22 (a later-described outer case 32) has a center axis C. For example, the transducer unit 24, the probe 26, and the sheath unit 28 are coupled to the handle unit 22 on the center axis C.

Figure 2:
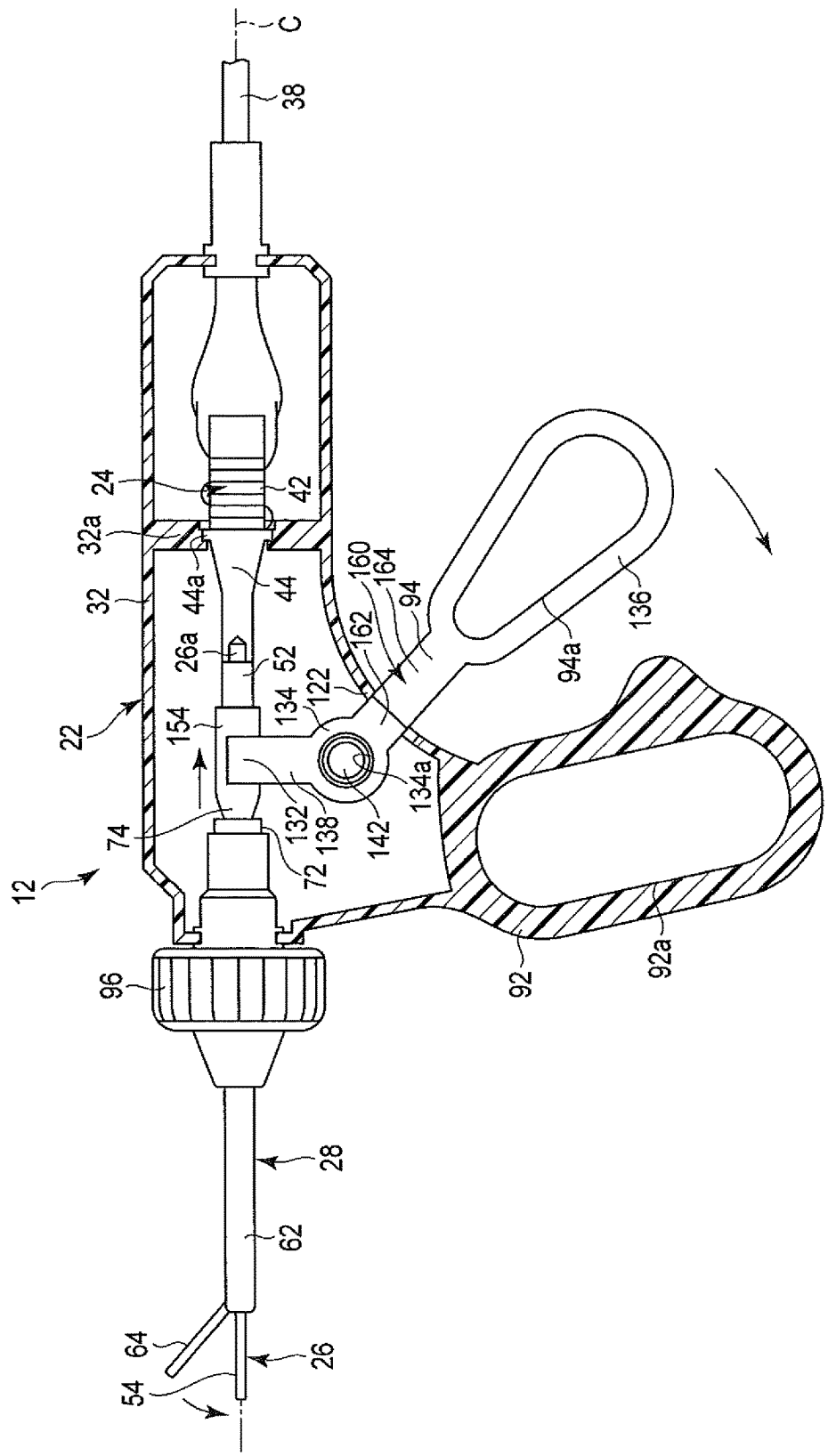
FIG. 2 is a cross-sectional view showing an internal configuration of the surgical device according to the first to third embodiments.

As shown in FIG. 2, the handle unit 22 for the surgical device 12 has the outer case (a handle main body) 32 having electrical insulating properties. The probe 26 and the transducer unit 24 arranged on a proximal end side of the probe 26 are supported in the outer case 32.

Figure 3:
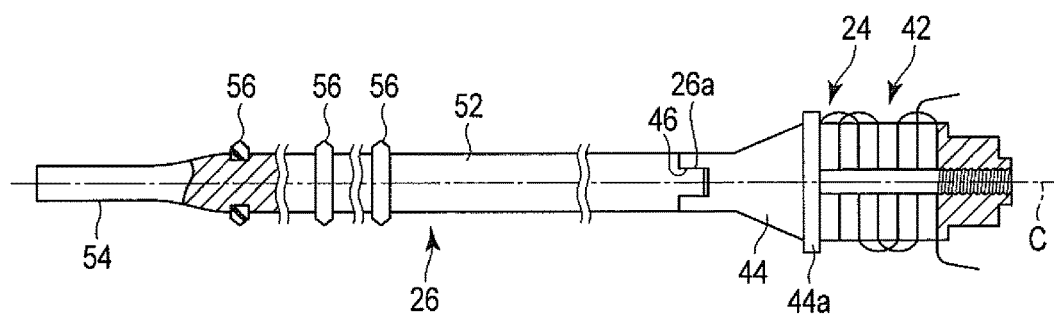
FIG. 3 is a schematic partial cross-sectional view showing an ultrasonic transducer unit and a probe connected to the transducer unit in the surgical device according to the first to third embodiments.

As shown in FIG. 2 and FIG. 3, the transducer unit 24 has an ultrasonic transducer 42 that generates ultrasonic vibration in response to supply of appropriate electricity from the controller 14 (see FIG. 1) and a conical horn 44 that expands an amplitude of the ultrasonic vibration generated in the ultrasonic transducer 42. The horn 44 is disposed to a male screw 26a at a proximal end of the probe 26 by a connection screw (a female screw) 46. The horn 44 includes an outer flange 44a protruding to the outside in a radial direction to the center axis C of the horn 44.

As shown in FIG. 2, an inner flange 32a inwardly protruding from an inner peripheral surface is formed on the outer case 32. When the outer flange 44a of the horn 44 engages with the inner flange 32a of the outer case 32, the transducer unit 24 is supported by the outer case 32.

It is to be noted that, in this embodiment, an example that the ultrasonic transducer unit 24 is supported in the outer case 32 will be described, but configuring the ultrasonic transducer unit 24 to be attachable to or detachable from the outer case 32 is also preferred.

A proximal end side of the outer case 32 is connected with a cable 38 through which signals are supplied or received to the controller 14 shown in FIG. 1 from later-described switches 102, 104, and others or electric power controlled by the controller 14 is supplied to the ultrasonic transducer 42.

The probe 26 shown in FIG. 3 is designed so that an entire length thereof becomes an integral multiple of a half wavelength of the ultrasonic vibration. The probe 26 has a rod-shaped probe main body 52 made of a metal such as a titanium alloy and a treatment section 54 provided on a distal end side of the probe main body 52. The ultrasonic vibration generated by the ultrasonic transducer 42 is subjected to amplitude expansion by the horn 44 and transmitted to the treatment section 54 via the probe main body 52. Vibration absorption members 56 are arranged on an outer peripheral surface of the probe main body 52 along the axial direction at several positions which are node positions of the vibration. The vibration absorption members 56 are made of a material having heat resisting properties and electric insulating properties, e.g., a PTFE material.

Figure 4:
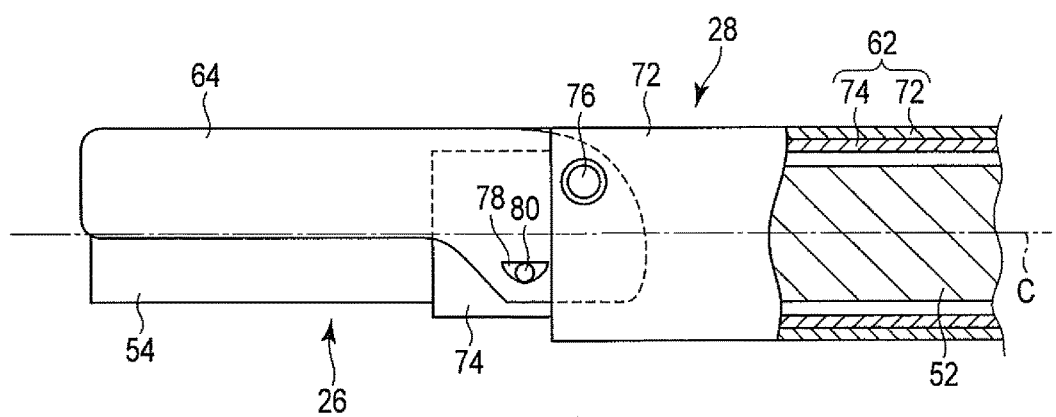
FIG. 4 is a partial cross-sectional view showing a configuration of a jaw and a treatment section of the probe in the surgical device according to the first to third embodiments.

As shown in FIG. 2 and FIG. 4, the sheath unit 28 has a sheath main body 62 formed of a cylindrical body and a jaw 64 as an end effector arranged on a distal end side of the sheath main body 62. The sheath main body 62 includes a cylindrical outer sheath 72 as an outer tube and a cylindrical drive pipe (a drive member) 74 as an inner tube. The drive pipe 74 is inserted into the outer sheath 72 to be slidable along the axial direction of the center axis C. The probe 26 is inserted through the drive pipe 74. The probe main body 52 and the drive pipe 74 are separated from each other by the vibration absorption members 56 (see FIG. 4).

A proximal end of the jaw 64 is supported at a distal end of the outer sheath 72 to allow its turning movement by a fulcrum pin 76. Further, at the time of assembling the probe 26 and the sheath unit 28, the jaw 64 is arranged at a position where it is confronted with the treatment section 54 of the probe 26.

The jaw 64 includes coupling pin supports 78 on both side portions of the proximal end portion thereof around the fulcrum pin 76. A coupling pin 80 that couples the jaw 64 with the drive pipe 74 is attached to the respective coupling pin supports 78. When the drive pipe 74 moves forward and backward in the axial direction, a drive force of the drive pipe 74 is transmitted to the jaw 64 through the coupling pin 80. Thus, the jaw 64 is turned around the fulcrum pin 76, and the jaw 64 is moved closer to or away from, namely, opened and closed to the treatment section 54. At this time, when the drive pipe 74 moves to the proximal end side, the jaw 64 moves in a direction to get closer to the treatment section 54, i.e., a direction to be closed. When the drive pipe 74 moves to the distal end side, the jaw 64 moves in a direction to get away from the treatment section 54, i.e., a direction to be opened.

As shown in FIG. 1, the handle unit 22 includes a fixed handle (a fixed member) 92 and a movable handle (a moving member) 94 that can move to the fixed handle 92. The handle unit 22 further includes a rotary operation knob 96 that enables the probe 26 and the sheath unit 28 to rotate in the periaxial direction of the center axis C.

In this embodiment, the fixed handle 92 includes a finger hook section (an annular portion) 92a for hooking, e.g., fingers except a thumb. It is to be noted that the finger hook section 92a does not necessarily have to be formed, and a front surface of the fixed handle 92 (a front side parallel to the center axis C) may be supported by the fingers other than the thumb.

As shown in FIG. 2, the fixed handle 92 is integrally formed on the outer case (the handle main body) 32 or fixed on the outer case 32. A plurality of switches 102 and 104 are arranged on an end surface of the fixed handle 92. When the switch 102 or 104 is selectively pressed, a treatment function (e.g., coagulation, incision, or the like) in the treatment section 54 of the probe 26 is selected.

FIG. 5 shows the probe main body 52 and a coupling section of the proximal end of the sheath unit 28 and the handle unit 22. As shown in FIG. 5, the rotary operation knob 96 is disposed to the outer case 32 to allow its turning movement in the periaxial direction around the center axis C of the outer sheath 72. The rotary operation knob 96 is arranged on an outer peripheral side of the outer sheath 72. The rotary operation knob 96 is integrally assembled to the probe main body 52, the drive pipe 74, and the outer sheath 72. Here, a coupling configuration of the rotary operation knob 96, the probe main body 52, the drive pipe 74, and the outer sheath 72 will now be described.

The rotary operation knob 96 has at its proximal end portion a pair of engagement claws 112 protruding toward the inner side. The outer sheath 72 has at its proximal end portion a pair of engagement holes 114 that engage with the engagement claws 112. When the engagement claws 112 of the rotary operation knob 96 engage with the engagement holes 114 of the outer sheath 72 respectively, the outer sheath 72 is disposed to the rotary operation knob 96. The drive pipe 74 has at its proximal end portion a pair of slide holes 116 in which the engagement claws 112 can relatively move. The slide holes 116 are formed into an elongated hole shape longer than a thickness of each engagement claw 112 along the axial direction of the probe main body 52 (a dimension of the probe main body 52 in the axial direction). When the engagement claws 112 are inserted into the slide holes 116 respectively, the drive pipe 74 is disposed to the rotary operation knob 96. Thus, when the drive pipe 74 is disposed to the rotary operation knob 96, the drive pipe 74 can move along the axial direction of the center axis C. The probe main body 52 has on its outer peripheral surface an engagement grove 118 that engages with the engagement claws 112. The engagement groove 118 is formed at a node position of the vibration. When the engagement claws 112 engage with the engagement groove 118, the probe main body 52 is supported by the rotary operation knob 96. As described above, the probe main body 52, the drive pipe 74, the outer sheath 72, and the rotary operation knob 96 are integrally assembled. Furthermore, when the rotary operation knob 96 is turned in the periaxial direction of the center axis C of the outer sheath 72, the outer sheath 72, the drive pipe 74, and the probe main body 52 in the outer case 32 are rotated in the periaxial direction of the center axis C together with the rotary operation knob 96. In conjunction with this operation, the jaw 64 of the sheath unit 28 and the treatment section 54 of the probe 26 are also rotated in the periaxial direction of the center axis C integrally with the outer sheath 72, the drive pipe 74, and the probe main body 52.

As shown in FIG. 2, the outer case 32 includes an opening 122 that defines a moving range of the movable handle 94 on the proximal end side of the fixed handle 92. The movable handle 94 has one end provided in the outer case 32 and the other end provided outside the outer case 32. The opening 122 can not only define a turning range in which the movable handle 94 is separated from the fixed handle 92 but also define a turning range of a later-described support section 136 depending on a position of a later-described coupling section 166.

In addition, it is preferable to arrange a non-illustrated elastic member such as a spring between the outer case 32 and the movable handle 94 so that the movable handle 94 is separated from the fixed handle 92. That is, it is preferable to arrange the movable handle 94 at a position in the opening 122 distant from the fixed handle 92 when it is not held by a user.

As shown in FIG. 2, the movable handle 94 includes an acting section 132 that acts on the drive pipe 74, a turning fulcrum 134 as a first coupling section coupled with the outer case 32, and the support section 136 supported by a user's thumb. It is to be noted that the acting section 132 is coupled with the turning fulcrum 134 through an arm 138.

The turning support 134 of the movable handle 94 has a fulcrum hole 134a at a central portion thereof. A turning pin 142 as a turning shaft is arranged in the fulcrum hole 134a of the turning support 134. It is preferable for an axial direction of the turning pin 142 to be orthogonal to the center axis C of the sheath unit 28. Thus, the movable handle 94 is disposed to the outer case 32 so that it can turn with the turning pin 142 of the turning fulcrum 134 as a supporting point. That is, the movable handle 94 can move closer to or away from the fixed handle 92 by the turning pin 142 arranged in the fulcrum hole 134a of the turning fulcrum 134. Moreover, when the movable handle 94 moves closer to or away from the fixed handle 92 in this manner, a turning plane S1 (see FIG. 7B) is defined.

Figure 7B:
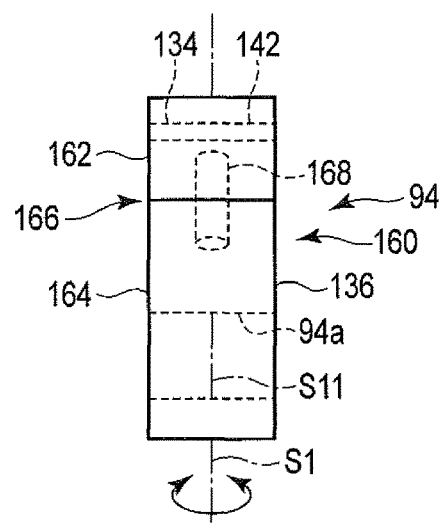
FIG. 7B is a schematic view showing a state that the movable handle is seen from a direction of an arrow 7B in FIG. 7A.

The support section 136 at the other end of the movable handle 94 has a finger hook section (an annular portion) 94a for hooking a user's thumb. In a state that fingers of one hand of the user are hooked in the finger hook sections 92a and 94a of the fixed handle 92 and the movable handle 94, when the movable handle 94 is turned around the turning pin 142, the movable handle 94 can be moved closer to or away from the fixed handle 92. It is to be noted that, as shown in FIG. 7B, in a neutral state that the support section 136 is not turned to the acting section 132, a discoid plane (a virtual plane) S11 is defined on the turning plane S1 of the finger hook section 94a of the movable handle 94 by an edge portion of the finger hook section 94a.

As shown in FIG. 6A and FIG. 6B, the acting section 132 is provided at one end of the movable handle 94 in this embodiment. The acting section 132 has a substantially-U-like U-shaped body 152 having a pair of claw sections 152a and 152b facing each other. As shown in FIG. 5 to FIG. 6B, the drive pipe 74 includes at its proximal end portion a large-diameter section 154 having an outer diameter larger than an outer diameter of any other portion of the drive pipe 74. The large-diameter section 154 is arranged on the proximal end side of the proximal end of the outer sheath 72. As shown in FIG. 6A and FIG. 6B, the large-diameter section 154 of the drive pipe 74 includes notch grooves 154a and 154b that engage with the claw sections 152a and 152b of the acting section 132. When the claw sections 152a and 152b engage with the notch grooves 154a and 154b and the U-shaped body 152 is disposed on the outer peripheral surface of the drive pipe 74, the movable handle 94 can be installed on the drive pipe 74, and the drive pipe 74 can be moved in conjunction with the turning movement of the movable handle 94.

That is, when the movable handle 94 is moved closer to or away from the fixed handle 92, an operating force is transmitted to the drive pipe 74 coupled with the U-shaped body 152 of the movable handle 94, and the drive pipe 74 moves along the axial direction of the center axis C. In conjunction with this movement of the drive pipe 74, the jaw 64 is moved closer to or away from the treatment section 54 of the probe 26, i.e., opened or closed. For example, when a closing operation to move the movable handle 94 closer to the fixed handle 92 is performed, the drive pipe 74 moves to the proximal end side along the center axis C. Thus, in conjunction with the movement of the drive pipe 74, the jaw 64 is closed to the treatment section 54 of the probe 26. On the other hand, when an opening operation to move the movable handle 94 away from the fixed handle 92 is performed, the drive pipe 74 moves toward the distal end side along the center axis C. Thus, in conjunction with the movement of the drive pipe 74, the jaw 64 is opened to the treatment section 54 of the probe 26.

As shown in FIG. 2, the turning fulcrum 134 and the support section 136 of the movable handle 94 are coupled with each other through a movable arm 160. As schematically shown in FIG. 7A and FIG. 7B, the movable arm 160 includes a first arm (a top handle) 162 that moves closer to the turning fulcrum 134, i.e., the turning pin 142, a second arm (a bottom handle) 164 that moves closer to the support section 136, and a coupling section (a second coupling section) 166 that couples the first arm 162 with the second arm 164. That is, the first arm 162 is integral with, e.g., the turning fulcrum 134, and the second arm 164 is integral with, e.g., the support section 136.

Here, a longitudinal axis (an extended axis defined by the turning fulcrum 134 and the support section 136) L is defined toward the support section 136 from the turning pin 142 that supports the movable handle 94 to allow its turning movement. The longitudinal axis L is present on the turning plane S1. The coupling section 166 has a turning shaft 168 that is orthogonal to the turning fulcrum 134 and the turning pin 142, arranged along the longitudinal axis L, and that schematically shows a later-described second turning body 174. Thus, the coupling section 166 can turn the support section 136 in a periaxial direction of the longitudinal axis L. That is, the second arm 164 can turn in the periaxial direction of the longitudinal axis L to the first arm 162 by the turning shaft 168. Therefore, the coupling section 166 can operate the discoid plane S11 of the finger hook section 94a of the movable handle 94 in the periaxial direction of the longitudinal axis L to deviate from the turning plane S1, thereby suppressing and alleviating a burden on a finger put in the finger hook section 94a of the movable handle 94.

It is to be noted that the coupling section 166 may be arranged inside or outside the outer case 32. When the coupling section 166 is arranged inside the outer case 32, the turning range of the support section 136 can be regulated by the edge portion of the opening 122.

Figure 8A:
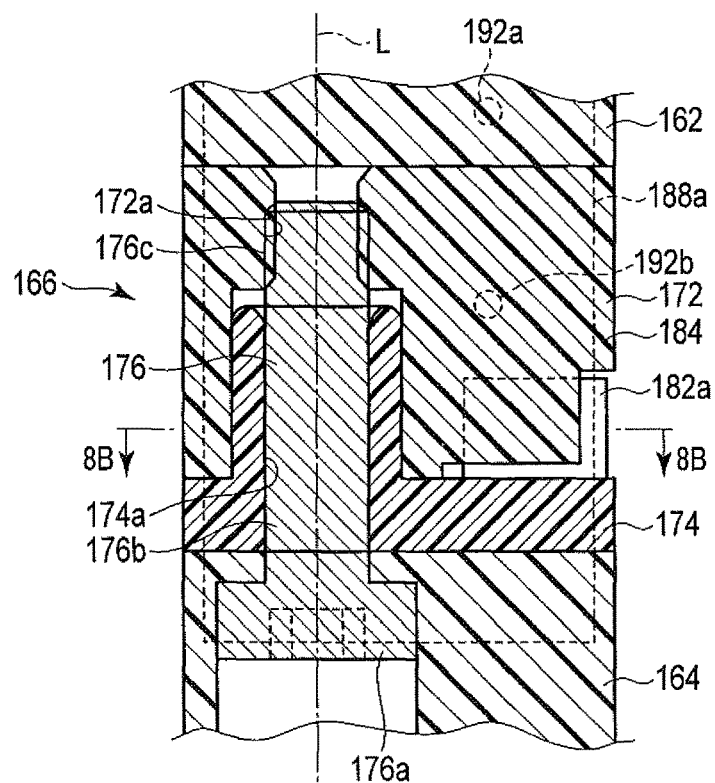
FIG. 8A is a schematic longitudinal sectional view showing first and second arms and a coupling section between them in the movable handle that is openable/closable to the fixed handle in the handle unit of the surgical device according to the first embodiment.
Figure 8B:
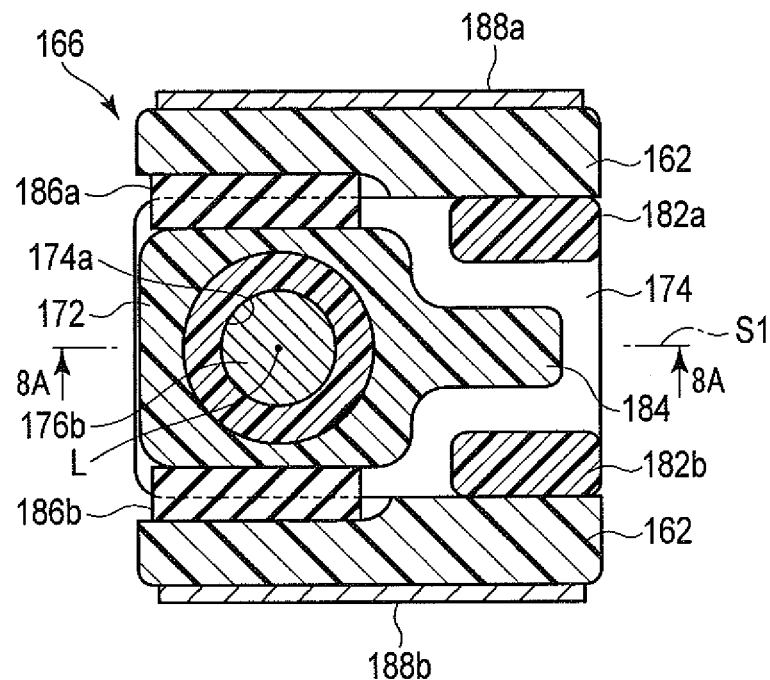
FIG. 8B is a schematic transverse sectional view taken along a line 8B-8B in FIG. 8A.

A specific configuration of the coupling section 166 will now be described with reference to FIG. 8A and FIG. 8B. As shown in FIG. 8A and FIG. 8B, the coupling section 166 includes a first turning body 172 that is coupled with the first arm 162 by later-described elastic members 188a and 188b such as leaf springs, a second turning body 174 as a turning shaft arranged between the second arm 164 and the first turning body 172, and a third turning body 176. In this embodiment, the third turning body 176 is formed as a bolt. The first turning body 172 and the second turning body 174 can relatively turn. Although not shown, it is also preferable to arrange a bearing such as a ball bearing between the first turning body 172 and the second turning body 174. Thus, the coupling section 166 can turn the support section 136 in the periaxial direction of the longitudinal axis L. That is, the second arm 164 can turn in the periaxial direction of the longitudinal axis L to the first arm 162 by the second turning body 174. Thus, the coupling section 166 can operate the discoid plane S11 of the finger hook section 94a of the movable handle 94 in the periaxial direction of the longitudinal axis L to deviate from the turning plane S1, thereby suppressing and alleviating a burden on a finger put in the finger hook section 94a of the movable handle 94.

The first turning body 172 has a female screw section 172a in which a later-described male screw section 176c of the third turning body 176 is screwed along the longitudinal axis L. It is to be noted that, in this embodiment, the third turning body 176 has a head section 176a, a shaft section 176b, and the male screw section 176c.

The second turning body 174 has a tubular section 174a in which the shaft section 176b of the third turning body 176 is inserted. It is preferable for the center axis of the tubular section 174a to coincide or substantially coincide with the longitudinal axis L. Further, it is preferable for the center axis of the tubular section 174a to be parallel or substantially parallel to the longitudinal axis L even though it does not coincide or substantially coincide with the longitudinal axis L. That is, the turning shaft 168 may coincide with the longitudinal axis L or may deviate from the longitudinal axis L. The second turning body 174 has a pair of regulating bodies 182a and 182b that regulate the turning movement in the periaxial direction of the tubular section 174a of the second turning body 174 to a predetermined range.

The first turning body 172 has a protruding section 184 that protrudes in a direction orthogonal to the center axis of the tubular section 174a of the second turning body 174, is arranged between the pair of regulating bodies 182a and 182b, and can abut on the pair of regulating bodies 182a and 182b. That is, the protruding section 184 of the first turning body 172 and the pair of regulating bodies 182a and 182b of the second turning body 174 form a turning regulating section that regulates a turning amount of the second arm 164 to the first arm 162.

A pair of buffer members 186a and 186b are arranged between the first arm 162 and the first turning member 172. These buffer members 186a and 186b are elastically deformable since they are made of a material having flexibility, e.g., silicone. These buffer members 186a and 186b elastically deform between the first turning body 172 and the first arm 162 when the second turning body 174 turns to the first turning body 172. Thus, these buffer members 186a and 186b are for maintaining a state in which the protruding section 184 of the first turning body 172 is arranged near the center of the regulating bodies 182a and 182b (a state that the discoid plane 811 of the finger hook section 94a of the support section 136 is present on the turning plane S1) and also suppress sudden movement of the second arm 164 to the first arm 162.

As shown in FIG. 8B, elastic members 188a and 188b such as leaf springs extended toward the second arm 164 are arranged on the first arm 162. The elastic members 188a and 188b couple the first arm 162 and the first turning body 172 by using fixing members 192a and 192b such as screws. These elastic members 188a and 188b exert an urging force to prevent the second arm 164 from twisting to the first arm 162. Thus, they are for maintaining a state in which the protruding section 184 of the first turning body 172 is arranged near the center of the regulating bodies 182a and 182b (a state that the discoid plane S11 of the finger hook section 94a of the support section 136 is present on the turning plane S1), and also suppress sudden movement of the second arm 164 to the first arm 162.

It is to be noted that at least either the buffer members 186a and 186b or the elastic members 188a and 188b are required to be provided. Thus, the coupling section 166 is for maintaining the plane S11 on the turning plane S1, while allowing the discoid plane S11 of the finger hook section 94a of the movable handle 94 to be away from the turning plane S1 with the buffer members 186a and 186b, the elastic members 188a and 188b, or the buffer members 186a and 186b as well as the elastic members 188a and 188b.

An operation of the surgical system 10 according to this embodiment will now be described.

In the surgical device 12 of the surgical system 10 according to this embodiment, a user's fingers except a thumb are hooked in the finger hook section 92a of the fixed handle 92 to support the fixed handle 92, and the thumb of the same hand of the user is hooked in the finger hook section 94a of the movable handle 94 to support the movable handle.

The movable handle 94 is moved closer to the fixed handle 92, i.e., operated to close. An operating force is transmitted to the drive pipe 74 coupled with the acting section 132 of the movable handle 94, and the drive pipe 74 moves forward in the axial direction. In conjunction with this operation, the jaw 64 moves closer to the treatment section 54 of the probe 26 and closes. In this state, the jaw 64 and the treatment section 54 of the probe 26 are inserted into a biological tissue of a treatment target in a narrow pore through, e.g., a non-illustrated trocar. Further, the user of the surgical device 12 arranges the jaw 64 and the treatment section 54 of the probe 26 to confront the biological tissue of the treatment target while supporting the fixed handle 92 and the movable handle 94. At this moment, the movable handle 94 may be separated from the fixed handle 92, and the jaw 64 may be separated from the treatment section 54 of the probe 26.

The rotary operation knob 96 is rotated in the periaxial direction of the center axis C of the sheath unit 28, and directions of the jaw 64 and the treatment section 54 of the probe 26 are appropriately adjusted to the biological tissue of the treatment target. Furthermore, the user moves the handle unit 22 while supporting the fixed handle 92 and the movable handle 94, thereby confronting the jaw 64 and the treatment section 54 of the probe 26 with the biological tissue of the treatment target. At this time, the user maintains a state that the jaw 64 and the treatment section 54 of the probe 26 are confronted with the biological tissue of the treatment target while directing a palm of a user's hand to a ceiling or directing a back of the hand to the ceiling. That is, the user moves the handle unit 22 in a positioned state without changing positions of a tip of the treatment section 54 of the probe 26 and a tip of the jaw 64. Namely, the user supports the fixed handle 92 and the movable handle 94 and maintains the tip of the treatment section 54 of the probe 26 and the tip of the jaw 64 in the positioned state.

Moreover, the movable handle 94 is moved closer to the fixed handle 92 to grasp the biological tissue of the treatment target between the jaw 64 and the treatment section 54 of the probe 26. When one of the switches 102 and 104 arranged on the front surface of the outer case 32 is pressed while maintaining this state, ultrasonic vibration is generated from the ultrasonic transducer 42 of the ultrasonic transducer unit 24, and a treatment assigned to the pressed switch is given.

Here, when the user's thumb comes into contact with the edge portion of the finger hook section 94a of the movable handle 94, a load in the periaxial direction of the longitudinal axis L is applied to the support section 136 of the movable handle 94. In such a case, the second arm 164 can turn the first arm 162 against the elastic force of the buffer members 186a and 186b and the urging force of the elastic members 188a and 188b. However, since the turning range of the second arm 164 to the first arm 162 is regulated by, e.g., the edge portion of the opening 122, the buffer members 186a and 186b, and the elastic members 188a and 188b, the second arm 164 can be prevented from being extremely turned to the first arm 162.

As described above, the handle unit 22 of the surgical device 12 according to this embodiment can not only move the movable handle 94 along the turning plane S1 (see FIG. 7B) defined by the turning movement of the turning pin 142 but also move the same while turning the support section 136 of the movable handle 94 with the use of the turning shaft 168 (the second turning body 174) when the user's thumb abuts on the finger hook section 94a of the movable handle 94. Thus, a burden imposed on the user's hand can be reduced.

Additionally, for example, the burden imposed on the hand varies depending on a state that the palm of the user's hand is directed to an upper side (a ceiling side) or a state that the back of the hand is directed to the upper side (the ceiling side) while grasping the handle unit 22 of the surgical device 12. Further, in the state that the palm of the hand is directed to the upper side or the state that the back of the hand is directed to the upper side, the burden imposed on the hand varies depending on a turning angle of a wrist. A state that the user directs the palm or the back of the hand to the upper side and the jaw 64 is allowed to approach the treatment section 54 of the probe 26 is kept for, e.g., several minutes in some situations. In this case, when the second arm 164 is turned in the periaxial direction of the longitudinal axis L to the first arm 162 at the time of operating the movable handle 94, the burden imposed on the user's hand can be reduced.

Furthermore, when there is kept the state that the movable handle 94 is allowed to come close to the fixed handle 92 without changing positions of the treatment section 54 of the probe 26 and the jaw 64, a turning amount of the second arm 164 to the first arm 162 can be changed from moment to moment by a force of the thumb that applies a load to the finger hook section 94a of the movable handle 94. That is, the turning amount of turning the second arm 164 of the movable handle 94 to the first arm 162 is changed depending on the amount by which the user's thumb abuts on the finger hook section 94a of the movable handle 94.

Thus, at the time of operating the movable handle 94, in a case of continuously keeping the movable handle 94 at a fixed position to the fixed handle 92, the burden imposed on the user can be reduced.

As described above, according to the surgical system 10 of this embodiment, the following can be said.

In the surgical device 12 of the surgical system 10 according to this embodiment, the support section 136 (the second arm 164) of the movable handle 94 can be turned in the periaxial direction of the turning shaft 168 (the second turning body 174) which is the periaxial direction of the center axis of the tubular section 174*a* of the second turning body 174 in this embodiment in accordance with a direction of the handle unit 22 grasped by the user.

That is, since the support section 136 of the movable handle 94 can be turned to the acting section 132, when the handle unit 22 is moved, the burden received by the user from the movable handle 94 can be suppressed and reduced. In a certain case, the user or the surgeon gives a treatment while continuously keeping the end effector (the jaw 64 in this embodiment) at a given position and while directing the palm or the back of the hand upward to change a direction of the entire handle unit 22 to various positions. Moving the entire handle unit 22 while maintaining (positioning) the end effector at a given position is very difficult since a burden is imposed on the user's hand. That is, in a case of giving a treatment to the same treatment target at various angles by using the end effector, a great burden is imposed on the user's hand with the movement of the entire handle, and hence this movement is a very difficult operation. According to the surgical device 12 of this embodiment, as different from, e.g., a device in which a direction of a fixed handle is adjustable, as disclosed in International Publication No. WO 2005/112795, an angle of the movable handle 94 can be adjusted in accordance with a burden on the thumb arranged in the finger hook section 94*a*. Thus, in a case of operating the movable handle 94 and in a case of operating the movable handle 94 and then maintaining this state, the burden imposed on the user's hand grasping the fixed handle 92 and the movable handle 94 can be further reduced. Therefore, in the surgical device 12 according to this embodiment, at the time of operating the movable handle 94 and at the time of operating the movable handle 94 and then maintaining this state, the burden is hardly imposed on the user, and an excellent operational feeling can be provided. Thus, the handle unit 22 can be easily moved without moving positions of the treatment section 54 of the probe 26 and the jaw 64, i.e., a position of the end effector as much as possible, and the state can be readily maintained after moving the handle unit 22. Therefore, at the time of operating the movable handle 94, when the handle unit 22 is, e.g., inclined by the user's operation, the support section 136 can be operated in a direction to deviate from the turning plane S1 in the coupling section 166. Consequently, the jaw 64 as the end effector can be easily held at a fixed position irrespective of the inclination of the handle unit 22.

Moreover, since the buffer members 186*a* and 186*b* are arranged between the first arm 162 and the first turning body 172, the protruding section 184 of the first turning body 172 can be continuously maintained between the pair of regulating bodies 182*a* and 182*b* of the second turning body 174. Thus, sudden turning of the second arm 164 to the first arm 162 is suppressed. Therefore, a great burden can be prevented from being suddenly imposed on the pair of regulating bodies 182*a* and 182*b* and the protruding section 184, and a maximum moving range of the second arm 164 to the first arm 162 can be defined.

Furthermore, by the operation of the pair of elastic members 188*a* and 188*b* such as leaf springs, a position of the second arm 164 to the first arm 162 can be urged to a neutral position (a position that the protruding section 184 of the first turning body 172 is arranged between the pair of regulating bodies 182*a* and 182*b* of the second turning body 174, i.e., a state that the turning plane S1 and the discoid plane S11 of the finger hook section 94*a* are present on the same plane). Thus, in the maximum moving range, a turning amount of the second arm 164 can be increased to the first arm 162 as the burden imposed on the user's thumb becomes large, and the turning amount of the second arm 164 can be reduced to the first arm 162 as the burden becomes small.

It is to be noted that the description has been given as to the example where the acting section 132 is arranged at one end of the movable handle 94 and the turning fulcrum 134 is arranged between the one end and the other end of the movable handle 94 in this embodiment. A position of the acting section 132 is not restricted to such a position, and reversing the positions of the turning fulcrum 134 and the acting section 132 is also preferable. That is, it is preferable to arrange the turning fulcrum 134 at the one end of the movable handle 94 and arrange the acting section 132 between the turning fulcrum 134 and the support section 136.

Moreover, in this embodiment, although the two coupling sections 134 and 166 are provided in the above description, the two coupling sections 134 and 166 may be formed as one coupling section by using, e.g., a universal joint.

A second embodiment will now be described with reference to FIG. 9A and FIG. 9B. This embodiment is a modification of the first embodiment, and like reference numerals denote the same members or members having the same functions as the members described in the first embodiment as much as possible to omit a detailed description thereof.

Figure 9A:
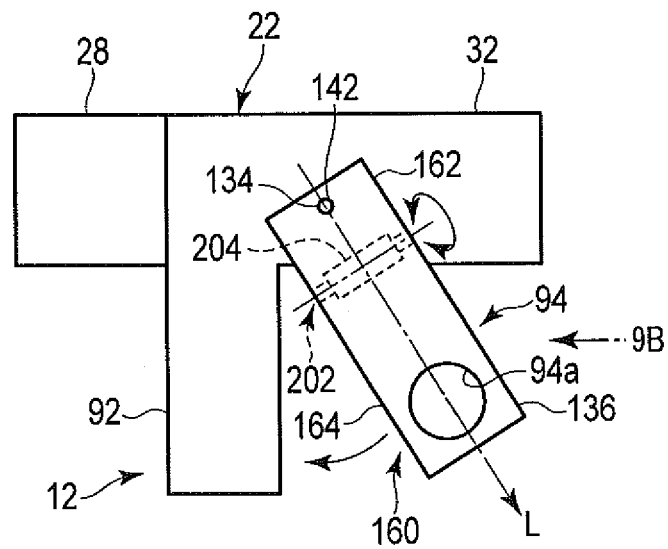
FIG. 9A is a schematic side view showing a configuration of the movable handle that is openable/closable to the fixed handle in the handle unit of the surgical device according to the second embodiment.

As schematically shown in FIG. 9A, a movable arm 160 of a movable handle 94 according to this embodiment includes a first arm (a top handle) 162 that moves closer to a turning fulcrum 134, i.e., a turning pin 142, a second arm (a bottom handle) 164 that moves closer to a support section 136, and a coupling section (a second coupling section) 202 that couples the first arm 162 with the second arm 164.

The coupling section 202 has a turning shaft 204 that is orthogonal to the turning fulcrum 134 and the turning pin 142 and likewise orthogonal to a longitudinal axis L. Therefore, the coupling section 202 can turn the support section 136 in a periaxial direction orthogonal to the longitudinal axis L. That is, the second arm 164 can turn in the periaxial direction orthogonal to the longitudinal axis L to the first arm 162 by the turning shaft 204. Thus, the coupling section 202 can operate the support section 136 to move on a turning plane S2 orthogonal to a turning plane S1 formed when the movable handle 94 moves to a fixed handle 92, and suppress and reduce a burden imposed on a finger put in a finger hook section 94*a* of the movable handle 94.

A turning range of the support section 136 with the turning shaft 204 as a fulcrum, i.e., a turning range of the second arm 164 is defined by, e.g., angles of abutting surfaces 206*a*, 206*b*, 208*a*, and 208*b* facing an axial direction of the turning shaft 204. Further, although not shown, in this embodiment, likewise, at least either buffer members 186*a* and 186*b* or elastic members 188*a* and 188*b* described in the first embodiment are arranged. Therefore, in a case that the support section 136 turns on the turning plane S2 away from the turning plane S1, the longitudinal axis L is to keep an arrangement state on the turning plane S1.

It is to be noted that the coupling section 202 may be arranged inside or outside an outer case 32. When the coupling section 202 is arranged in the outer case 32, the turning range of the support section 136 can be defined by an edge portion of an opening 122.

In a surgical device 12 of a surgical system 10 according to this embodiment, the movable handle 94 can turn in the periaxial direction of the turning shaft 204 in accordance with a direction of a handle unit 22 grasped by a user. That is, like the description of the first embodiment, since the support section 136 of the movable handle 94 can turn to an acting section 132, it is possible to suppress and reduce a burden imposed on the user from the movable handle 94 when the handle unit 22 is moved.

In the surgical device 12 according to this embodiment, at the time of operating the movable handle 94 and at the time of operating the movable handle 94 and then maintaining this state, the burden imposed on the user's hand can be further reduced and suppressed. Thus, in the surgical device 12 according to this embodiment, at the time of operating the movable handle 94 and at the time of operating the movable handle 94 and then maintaining this state, the burden can be hardly imposed on the user, and an excellent operational feeling can be provided. Therefore, the handle unit 22 can be easily moved without moving positions of a treatment section 54 of a probe 26 and a jaw 64, i.e., a position of an end effector as much as possible, and the handle unit 22 can be moved and then this state can be readily maintained. Thus, at the time of operating the movable handle 94, when the handle unit 22 is, e.g., inclined by the user's operation, the support section 136 of the coupling section 202 can be operated in a direction to deviate from the turning plane S1. Therefore, the jaw 64 as the end effector can be easily held at a fixed position irrespective of the inclination of the handle unit 22.

It is to be noted that, in this embodiment, the turning shaft 204 of the coupling section 202 can turn in the periaxial direction orthogonal to the longitudinal axis L, but this direction is not restricted to the orthogonal direction as long as it deviates from the longitudinal axis L.

A third embodiment will now be described with reference to FIG. 10A and FIG. 10B. This embodiment is a modification of the first and second embodiments, and like reference numerals denote the same members or members having the same functions as the members described in the first and second embodiments as much as possible to omit a detailed description thereof.

Figure 9B:
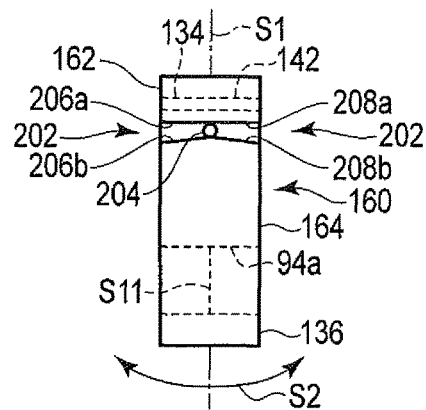
FIG. 9B is a schematic view showing a state that the movable handle is seen from a direction of an arrow 9B in FIG. 9A.
Figure 10A:
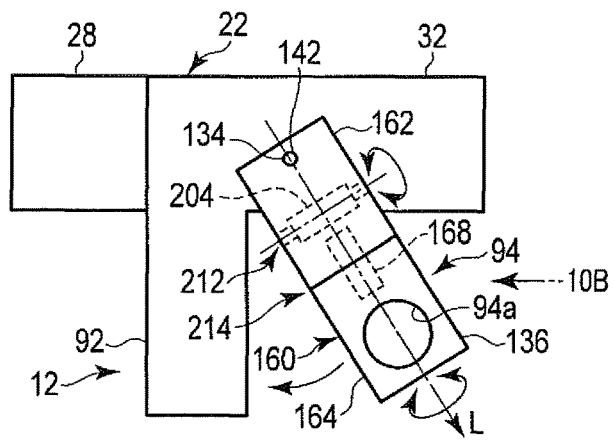
FIG. 10A is a schematic side view showing a configuration of the movable handle that is openable/closable to the fixed handle in the handle unit of the surgical device according to the third embodiment.
Figure 10B:
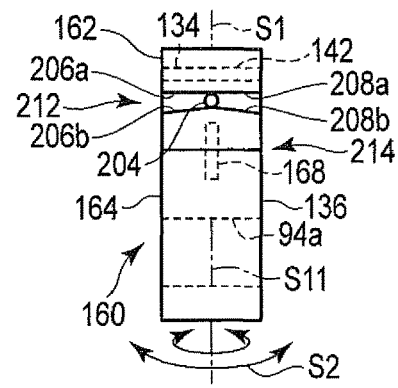
FIG. 10B is a schematic view showing a state that the movable handle is seen from a direction of the arrow 10B in FIG. 10A.

As schematically shown in FIG. 10A and FIG. 10B, a movable arm 160 of a movable handle 94 according to this embodiment includes a first arm (a top handle) 162 that moves closer to a turning fulcrum 134, i.e., a turning pin 142, a second arm (a bottom handle) 164 that moves closer to a support section 136, and coupling sections 212 and 214 that couple the first arm 162 with the second arm 164. That is, the movable handle 94 has the two coupling sections 212 and 214. Here, the coupling section 212 has the same configuration as the coupling section 202 (see FIG. 9A and FIG. 9B) described in the second embodiment, and the coupling section 214 has the same configuration as the coupling section 166 (see FIG. 7A and FIG. 7B) described in the first embodiment. That is, one coupling section (a second coupling section) 212 can turn the second arm 164 in a periaxial direction orthogonal to a longitudinal axis L to the first arm 162 by a turning shaft 204. The other coupling section (a third coupling section) 214 can turn the second arm 164 in the periaxial direction along the longitudinal axis L to the first arm 162 by a turning shaft 168. It is to be noted that, as a specific configuration of the coupling section 214, for example, a configuration shown in FIG. 8A and FIG. 8B can be adopted.

Therefore, according to a surgical device 12 of this embodiment, the support section 136 can be turned to an acting section 132 in the periaxial direction of the longitudinal axis L by the turning shaft 168 (see FIG. 7A and FIG. 7B) and in the periaxial direction of the axis orthogonal to the longitudinal axis L by the turning shaft 204 (see FIG. 9A and FIG. 9B) in predetermined ranges, respectively. Thus, it is possible to further increase a degree of freedom in a moving range of the movable handle 94 of the handle unit 22 described in the first embodiment and the second embodiment. Therefore, the surgical device 12 according to this embodiment can provide a more excellent operational feeling than the surgical device 12 described in the first and second embodiments.

Accordingly, the surgical device 12 according to this embodiment can facilitate moving a handle unit 22 without moving positions of a treatment section 54 of a probe 26 and a jaw 64, i.e., a position of an end effector as much as possible. Further, after moving the handle unit 22, this state can be easily maintained. Thus, at the time of operating the movable handle 94, when the handle unit 22 is, e.g., inclined by a user's operation, the coupling sections 212 and 214 can operate the support section 136 in a direction to deviate from a turning plane S1. Therefore, the jaw 64 as the end effector can be readily held at a fixed position irrespective of the inclination of the handle unit 22.

It is to be noted that, in this embodiment, the description has been given as to the example where the turning shaft 204 orthogonal to the longitudinal axis L is arranged on a side close to the turning fulcrum 134 along the longitudinal axis L and the turning shaft 168 parallel to the longitudinal axis L is arranged on a side apart from the turning fulcrum 134 along the same. As described in a ninth embodiment (see FIG. 18), it is also preferable to reverse arrangements of these turning shafts 168 and 204.

Furthermore, in this embodiment, the turning shaft 204 of the coupling section 214 can turn in the periaxial direction orthogonal to the longitudinal axis L, but this direction is not restricted to the orthogonal direction as long as it deviates from the longitudinal axis L.

Figure 11:
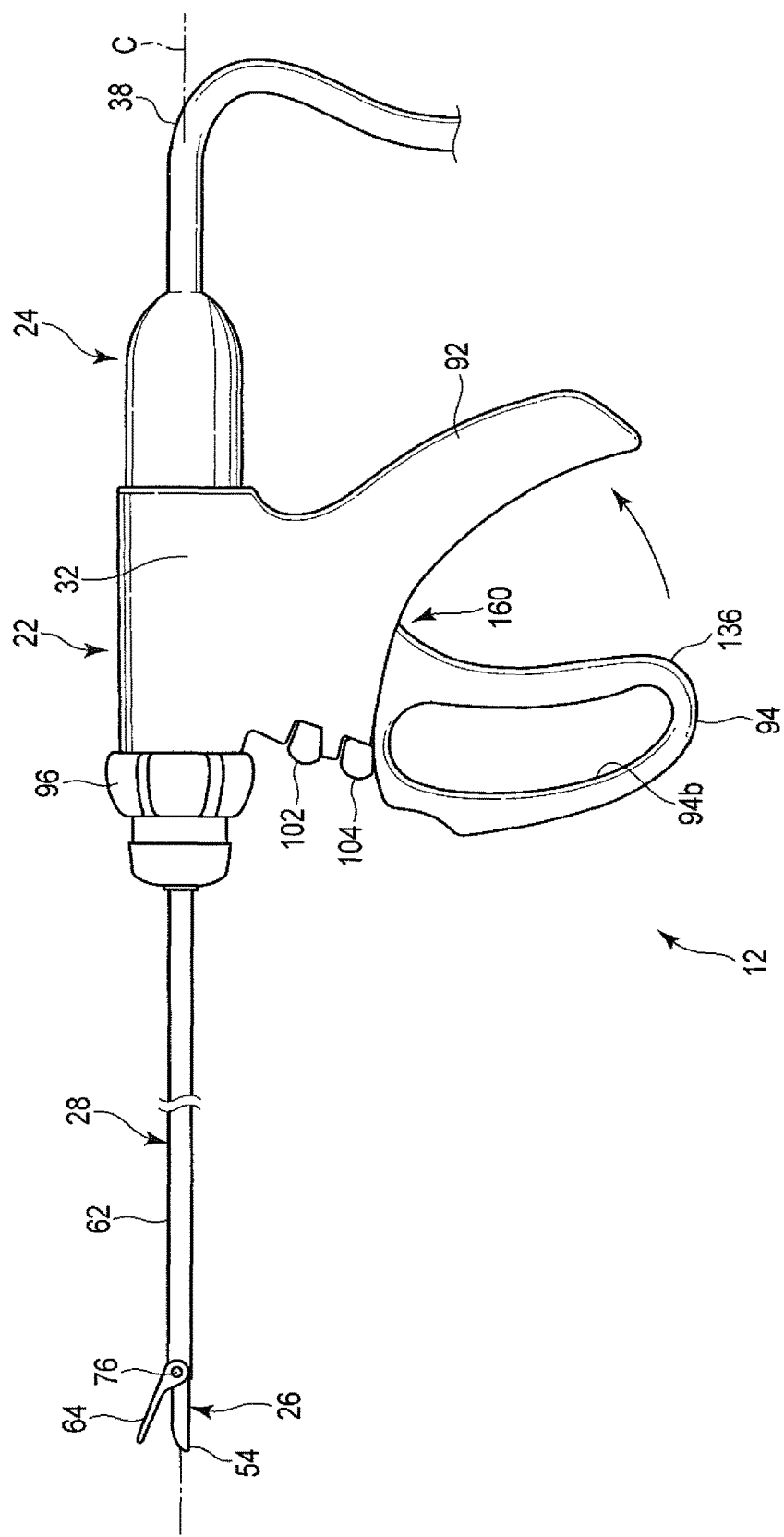
FIG. 11 is a schematic side view showing a surgical device according to a fourth embodiment.

A fourth embodiment will now be described with reference to FIG. 11 and FIG. 12. This embodiment is a modification of the first to third embodiments, and like reference numerals denote the same members or members having the same functions as the members described in the first to third embodiments as much as possible to omit a detailed description thereof.

In a surgical device 12 according to this embodiment, an ultrasonic transducer unit 24, a probe 26, and a sheath unit 28 are attachable to or detachable from an outer case 32. In this embodiment, the shape of the handle unit 22 described in the first to third embodiments is modified. As the handle unit according to the first to third embodiments, the description has been given as to the example where the fixed handle 92 is arranged on the front side along the center axis C and the movable handle 94 is arranged on the rear side along the same. On the other hand, in a handle unit 22 according to this embodiment, a movable handle 94 is arranged on a front side along a center axis C and a fixed handle 92 is arranged on a rear side along the same.

A thumb is hooked on a back side of the fixed handle 92, and a finger hook section is eliminated in this embodiment. Thus, the fixed handle 92 does not necessarily require the finger hook section. A finger hook section (an annular portion) 94b for hooking fingers except the thumb is formed in a support section 136 of the movable handle 94. Therefore, in the handle unit 22 according to this embodiment, the fixed handle 92 is supported by the thumb or a portion near a base of the thumb, and the finger hook section 94b of the movable handle 94 is supported when the fingers except the thumb are hooked therein.

It is to be noted that, in the finger hook section 94b of the movable handle 94, a discoid plane (a virtual plane) S11 is defined on a turning plane S1 by an edge portion of the finger hook section 94b in a neutral state that the support section 136 is not turned to an acting section 132.

Moreover, a jaw 64 moves closer to a treatment section 54 of the probe 26 when the movable handle 94 is moved closer to the fixed handle 92, and the jaw 64 moves away from the treatment section 54 of the probe 26 when the support section 136 of the movable handle 94 is moved away from the fixed handle 92. In this manner, the turning plane S1 is defined to the handle unit 22 of the surgical device 12. It is to be noted that a mechanism that enables the surgical device 12 to operate in this manner is well known, and a detailed description of the mechanism will be omitted.

Figure 12:
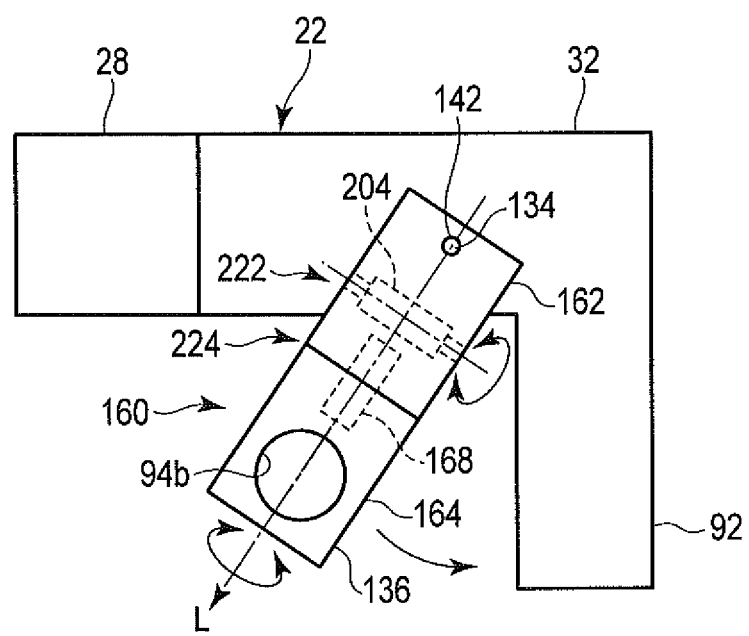
FIG. 12 is a schematic side view showing a configuration of a movable handle that is openable/closable to a fixed handle in a handle unit of the surgical device according to the fourth embodiment.

As schematically shown in FIG. 12, a movable arm 160 of the movable handle 94 according to this embodiment includes a first arm (a top handle) 162 that moves closer to a turning fulcrum 134, i.e., a turning pin 142, a second arm (a bottom handle) 164 that moves closer to the support section 136, and coupling sections 222 and 224 that couple the first arm 162 with the second arm 164. That is, the movable handle 94 has the two coupling sections 222 and 224. Here, the coupling section 222 has the same configuration as the coupling section 202 (see FIG. 9A and FIG. 9B) described in the second embodiment, and the coupling section 214 has the same configuration as the coupling section 166 (see FIG. 7A and FIG. 7B) described in the first embodiment. That is, one coupling section (a second coupling section) 222 can turn the second arm 164 in a periaxial direction orthogonal to a longitudinal axis L to the first arm 162 by a turning shaft 204. The other coupling section (a third coupling section) 224 can turn the second arm 164 in the periaxial direction parallel to the longitudinal axis L to the first arm 162 by a turning shaft 168. Thus, the coupling sections 222 and 224 can operate the support section 136 in such a manner that the discoid plane S11 of the finger hook section 94b of the movable handle 94 deviates from the turning plane S1 of the movable handle 94.

Therefore, according to the surgical device 12 of this embodiment, the support section 136 can be turned to the acting section 132 in the periaxial direction of the longitudinal axis L by the turning shaft 168 (see FIG. 7A and FIG. 7B) and in the periaxial direction of the axis orthogonal to the longitudinal axis L by the turning shaft 204 (see FIG. 9A and FIG. 9B) in predetermined ranges, respectively. Thus, as described in the third embodiment, it is possible to further increase a degree of freedom in a moving range of the movable handle 94 of the handle unit 22 described in the first embodiment and the second embodiment.

In the surgical device 12 of the surgical system 10 according to this embodiment, the support section 136 (the second arm 164) of the movable handle 94 can be turned in the periaxial directions of the turning shafts 168 and 204 in accordance with a direction of the handle unit 22 grasped by the user. That is, since the support section 136 of the movable handle 94 can be turned to the acting section 132, a burden received by the user from the movable handle 94 can be suppressed and alleviated when the handle unit 22 is moved.

In a certain case, the user, i.e., the surgeon gives a treatment while maintaining an end effector (the jaw 64 of the sheath unit 28 in this embodiment) at a given position and while directing the palm or the back of the hand upward to change a direction of the entire handle unit 22 to various positions. Moving the entire handle 22 while maintaining the end effector at a given position imposes a burden on the user's hand, and hence it is very difficult. That is, at the time of giving a treatment to the same treatment target at various angles by using the end effector, a considerable burden is imposed on the user's hand with movement of the entire handle, and hence it is a difficult operation. According to the surgical device 12 of this embodiment, as different from, e.g., a device in which a direction of the fixed handle 92 is adjustable, as disclosed in International Publication No. WO 2005/112795, an angle of the movable handle 94 can be adjusted in accordance with a burden on the fingers except the thumb arranged in the finger hook section 94b. Thus, in a case of operating the movable handle 94 and in a case of operating the movable handle 94 and then maintaining this state, the burden imposed on the user's hand can be further reduced and suppressed. Therefore, in the surgical device 12 according to this embodiment, at the time of operating the movable handle 94 and at the time of operating the movable handle 94 and then maintaining this state, the burden is hardly imposed on the user, and an excellent operational feeling can be provided. Thus, the handle unit 22 can be easily moved without moving positions of the treatment section 54 of the probe 26 and the jaw 64, i.e., a position of the end effector as much as possible, and the state can be readily maintained after moving the handle unit 22.

It is to be noted that, in this embodiment, the description has been given as to the example where the turning shaft 204 orthogonal to the longitudinal axis L is arranged on a side close to the turning fulcrum 134 along the longitudinal axis L and the turning shaft 168 parallel to the longitudinal axis L is arranged on a side apart from the turning fulcrum 134 along the same. As described in the ninth embodiment (see FIG. 18), it is also preferable to reverse arrangements of these turning shafts 168 and 204. Further, as described in the first and second embodiments, arranging one of the turning shafts 168 and 204 alone is also preferable.

Figure 13:
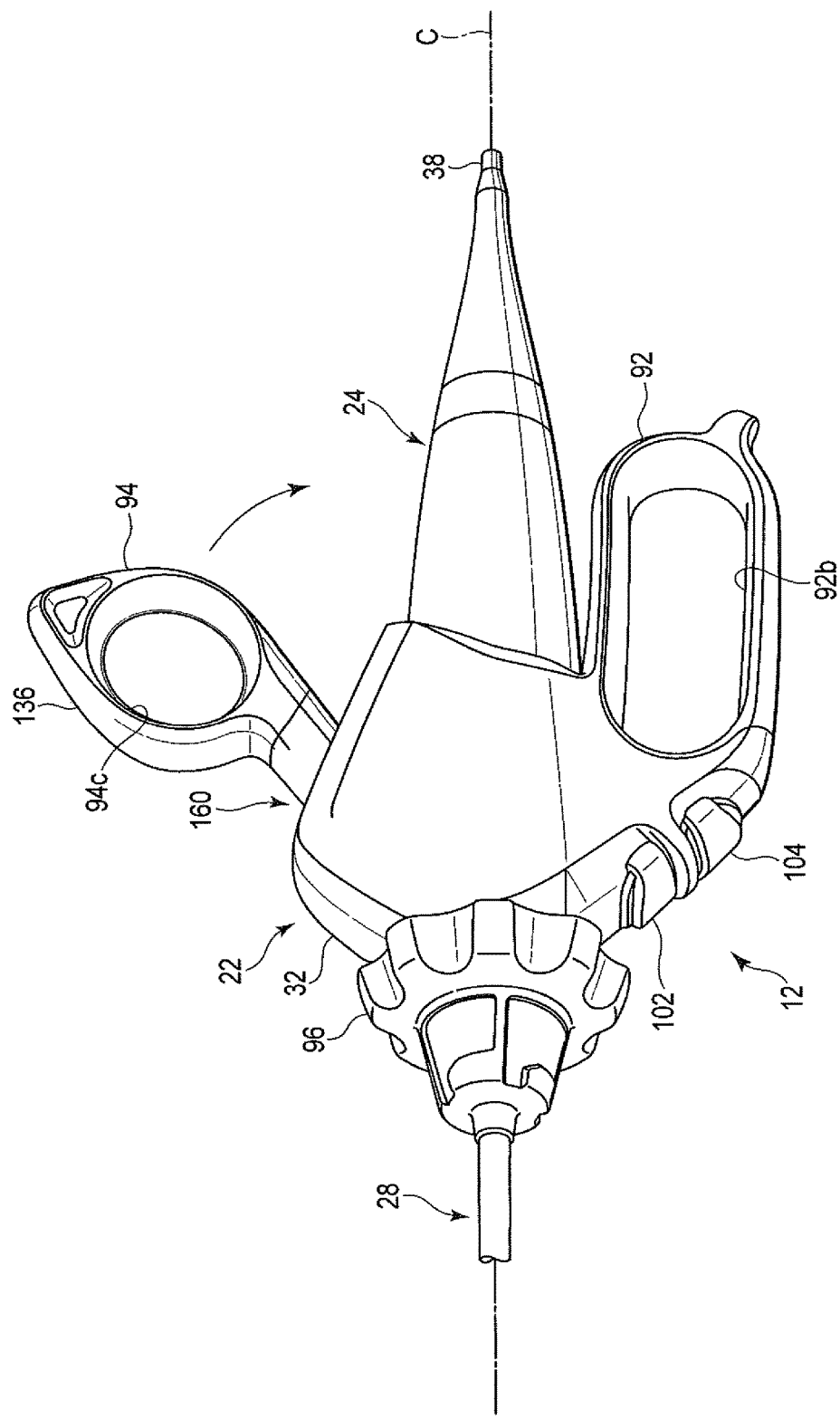
FIG. 13 is a schematic perspective view showing a surgical device according to a fifth embodiment.

A fifth embodiment will now be described with reference to FIG. 13 and FIG. 14. This embodiment is a modification of the first to fourth embodiments, and like reference numerals denote the same members or members having the same functions as the members described in the first to fourth embodiments to omit a detailed description.

In a surgical device 12 according to this embodiment, an ultrasonic transducer unit 24, a probe 26 (not shown), and a sheath unit 28 are attachable to or detachable from an outer case 32.

In this embodiment, the shape of the handle unit 22 described in the first to fourth embodiments is modified. As the handle unit 22 according to the first to fourth embodiments, the description has been given as to the example, where the fixed handle 92 and the movable handle 94 are arranged on one side on one side of the center axis C. On the other hand, in a handle unit 22 according to this embodiment, a fixed handle 92 and a movable handle 94 are arranged on opposite sides to sandwich a center axis C therebetween.

The fixed handle 92 has a finger hook section 92b in this embodiment. A finger hook section (an annular portion) 94c for hooking fingers except a thumb is formed in a support section 136 of the movable handle 94. In the handle unit 22 according to this embodiment, the finger hook section 92b of the fixed handle 92 is caught with the fingers except the thumb and the finger hook section 94c of the movable handle 94 is caught with the thumb and supported. It is to be noted that a discoid plane (a virtual plane) S11 is defined on a turning plane S1 to the finger hook section 94c of the movable handle 94 by an edge portion of the finger hook section 94c in a neutral state that a support section 136 does not turn to an acting section 132.

Further, when the movable handle 94 is moved closer to the fixed handle 92, a jaw 64 moves closer to a treatment section 54 of the probe 26 and when the support section 136 of the movable handle 94 is moved away from the fixed handle 92, the jaw 64 moves away from the treatment section 54 of the probe 26. In this manner, the turning plane S1 is defined on the handle unit 22 of the surgical device 12. It is to be noted that a mechanism that enables the surgical device 12 to operate in this manner is well known, and a detailed description of the mechanism will be omitted.

As schematically shown in FIG. 14, a movable arm 160 of the movable handle 94 according to this embodiment includes a first arm (a top handle) 162 that moves closer to a turning fulcrum 134, i.e., a turning pin 142, a second arm (a bottom handle) 164 that moves closer to the support section 136, and coupling sections 232 and 234 that couple the first arm 162 with the second arm 164. That is, the movable handle 94 has the two coupling sections 232 and 234. Each of the coupling sections 232 and 234 has the same configuration as the coupling section 202 (see FIG. 9A and FIG. 9B) described in the second embodiment. Here, one coupling section 232 has a turning shaft 242 having the same configuration as the turning shaft 204 described in the second embodiment, and the other coupling section 234 has a turning shaft 244 having the same configuration as the turning shaft 204 described in the second embodiment. It is to be noted that, in FIG. 14, axial directions of the turning shafts 242 and 244 are orthogonal to each other, but do not necessarily have to be orthogonal.

The one coupling section (a second coupling section) 232 can move the second arm 164 to a position away from the turning plane S1 to the first arm 162 by the turning shaft 242. Similarly, the other coupling section (a third coupling section) 234 can move the second arm 164 to a position away from the turning plane S1 to the first arm 162 by the turning shaft 244. Therefore, the coupling sections 232 and 234 can operate the support section 136 so that the discoid plane S11 of the finger hook section 94c of the movable handle 94 deviates from the turning plane S1 of the movable handle 94.

Therefore, according to the surgical device 12 of this embodiment, the support section 136 can be turned to the acting section 132 in a predetermined range by each of the turning shafts 242 and 244. Thus, as described in the third and fourth embodiments, it is possible to further increase a degree of freedom in a moving range of the movable handle 94 of the handle unit 22 described in the first embodiment and the second embodiment.

In the surgical device 12 of a surgical system 10 of the present embodiment, the support section 136 (the second arm 164) of the movable handle 94 can be turned in periaxial directions of the turning shafts 242 and 244 in accordance with a direction of the handle unit 22 grasped by a user. That is, the support section 136 of the movable handle 94 can be turned to the acting section 132, and hence at the time of moving the handle unit 22, a burden received from the movable handle 94 by the user can be suppressed and alleviated.

In a certain case, the user, i.e., a surgeon gives a treatment while maintaining an end effector (the jaw 64 of the sheath unit 28 in this embodiment) at a given position and while directing a palm or a back of a hand upward to change the direction of the entire handle unit 22 to various positions. It imposes a burden on the user's hand to move the entire handle 22 while maintaining the end effector at the given position, and hence it is very difficult. That is, at the time of giving the treatment to the same treatment target at various angles with the use of the end effector, a considerable burden is imposed on the user's hand with movement of the entire handle, and hence it is a difficult operation. According to the surgical device 12 of this embodiment, as different from, e.g., a device in which a direction of the fixed handle 92 is adjustable, as disclosed in International Publication No. WO 2005/112795, an angle of the movable handle 94 can be adjusted in accordance with a burden on the thumb arranged in the finger hook section 94c. Thus, in a case of operating the movable handle 94 and in a case of operating the movable handle 94 and then maintaining this state, the burden imposed on the user's hand can further be alleviated and suppressed. Therefore, in the surgical device 12 according to this embodiment, at the time of operating the movable handle 94 and at the time of operating the movable handle 94 and then maintaining this state, the burden is hardly imposed on the user, and an excellent operational feeling can be provided. Thus, the handle unit 22 can be easily moved without moving positions of the treatment section 54 of the probe 26 and the jaw 64, i.e., a position of the end effector as much as possible, and the state can be readily maintained after moving the handle unit 22.

It is to be noted that, in this embodiment, as described in the first and second embodiments, arranging one of the turning shafts 242 and 244 alone is also preferable.

A sixth embodiment will now be described with reference to FIG. 15. This embodiment is a modification of the first to fifth embodiments, and like reference numerals denote the same members or members having the same functions as the members described in the first to fifth embodiments as much as possible to omit a detailed description.

As schematically shown in FIG. 15, a movable arm 160 of a movable handle 94 according to this embodiment includes a first arm (a top handle) 162 that moves closer to a turning fulcrum 134, i.e., a turning pin 142, a second arm (a bottom handle) 164 that moves closer to a support section 136, and coupling sections 252 and 254 that couple the first arm 162 with the second arm 164. That is, the movable handle 94 has the two coupling sections 252 and 254. Each of the coupling sections 252 and 254 has the same configuration as the coupling section 166 (see FIG. 7A and FIG. 7B) described in the first embodiment. Here, one coupling section 252 has a turning shaft 262 having the same configuration as the turning shaft 168 described in the first embodiment, and the other coupling section 254 has a turning shaft 264 having the same configuration as the turning shaft 168 described in the first embodiment. It is to be noted that, in FIG. 15, axial directions of the turning shafts 262 and 264 are orthogonal to each other, but do not necessarily have to be orthogonal.

One coupling section (a second coupling section) 252 can operate, to the first arm 162 by the turning shaft 262, a finger hook section 94c having a plane defined by an edge portion thereof similarly to a turning plane S1 so that the finger hook section deviates from the turning plane S1, i.e., can move the second arm 164 to a position away from the turning plane S1. The other coupling section (a third coupling section) 254 can operate, to the first arm 162 by the turning shaft 264, the finger hook section 94c having the plane defined by the edge portion similarly to the turning plane S1 so that the finger hook section deviates from the turning plane S1, i.e., can move the second arm 164 to a position away from the turning plane S1. Therefore, the coupling sections 252 and 254 can operate the support section 136 so that a discoid plane S11 of the finger hook section 94c of the movable handle 94 deviates from the turning plane S1 of the movable handle 94.

Therefore, according to a surgical device 12 of this embodiment, the support section 136 can be turned to an acting section 132 in a predetermined range by each of the turning shafts 262 and 264. Thus, as described in the third to fifth embodiments, it is possible to further increase a degree of freedom in a moving range of the movable handle 94 of the handle unit 22 described in the first embodiment and the second embodiment.

In the surgical device 12 of a surgical system 10 of the present embodiment, as described in the fifth embodiment, the support section 136 (the second arm 164) of the movable handle 94 can be turned in periaxial directions of the turning shafts 262 and 264 in accordance with a direction of the handle unit 22 grasped by a user. That is, the support section 136 of the movable handle 94 can be turned to the acting section 132, and hence at the time of moving the handle unit 22, a burden received from the movable handle 94 by the user can be suppressed and alleviated.

It is to be noted that, in this embodiment, as described in the first and second embodiments, arranging one of the turning shafts 262 and 264 alone is also preferable.

A seventh embodiment will now be described with reference to FIG. 16. This embodiment is a modification of the first to sixth embodiments, especially a modification of the fifth and sixth embodiments, and like reference numerals denote the same members or members having the same functions as the members described in the first to sixth embodiments to omit a detailed description.

A surgical device 12 of this embodiment includes a handle unit 22, an ultrasonic transducer unit 24, and a probe 26. The handle unit 22 has a center axis C. For example, the transducer unit 24 and the probe 26 are coupled to the handle unit 22 on the center axis C.

In this embodiment, the sheath unit 28 (see FIG. 1 to FIG. 5) is eliminated. That is, in the surgical device 12 according to this embodiment, a drive pipe 74 is eliminated. An outer case 32 of the handle unit 22 has a sheath 28a that simply covers an outer periphery of a probe main body 52 of the probe 26, in place of the sheath unit 28 having the drive pipe 74. The sheath 28a is formed integrally with the outer case (a handle main body) 32 or fixed to a tip of the outer case 32.

Figure 16:
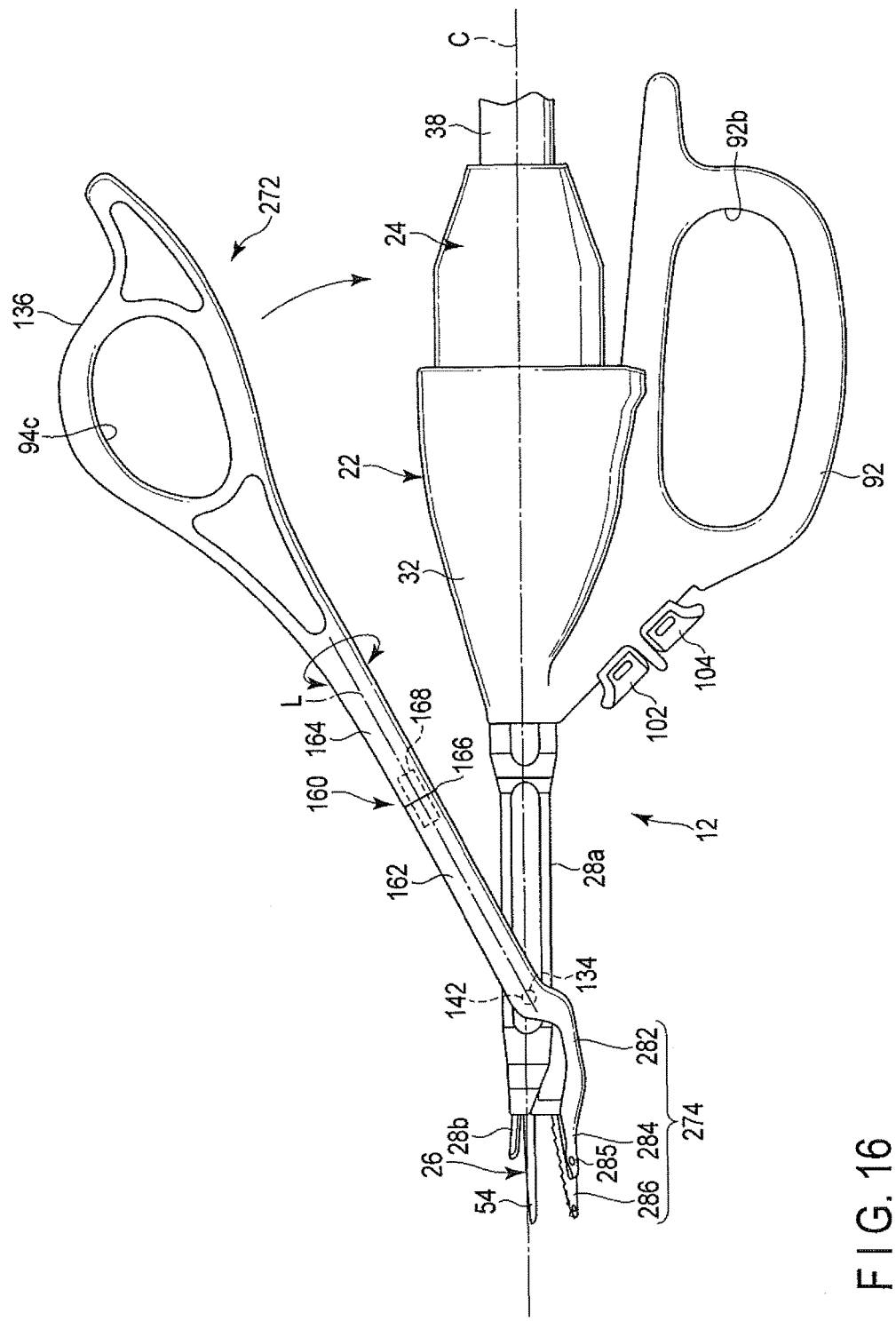
FIG. 16 is a schematic view showing a surgical device according to a seventh embodiment.

As shown in FIG. 16, the handle unit 22 includes a fixed handle (a fixed member) 92 and a movable handle (a moving member) 272 that can move closer to and away from the fixed handle 92. The movable handle 272 moves closer to and away from the fixed handle 92, thereby defining a turning plane S1.

The fixed handle 92 is formed integrally with the outer case (the handle main body) 32, or fixed to the outer case 32. Switches 102 and 104 are arranged on a front surface side of the fixed handle 92. When the switch 102 or 104 is selectively pressed, a treatment function (e.g., coagulation, incision, or the like) in a treatment section 54 of the probe 26 is selected.

The movable handle 272 according to this embodiment has an acting section 274 as an end effector that is movable closer to or away from, namely, openable or closable to the treatment section 54 of the probe 26, a turning fulcrum 134 as a first coupling section that is coupled with the handle unit 22, and a support section 136 that is supported by a user's thumb.

The acting section 274 of the movable handle 272 has a curved portion 282, a pedestal 284 and a jaw 286 in order from a side close to the turning fulcrum 134 toward a distal side. The curved portion 282 is formed to avoid interference with the sheath 28a, when the movable handle 272 moves closer to and away from the fixed handle 92. The pedestal 284 is present at a position that faces the treatment section 54 of the probe 26. The jaw 286 is supported to be swingable to the pedestal 284 via a pin 285. Thus, the jaw 286 can be displaced between a closed state that the jaw comes close to or abuts on the treatment section 54 of the probe 26 and an opened state that the jaw is separated from the treatment section 54 of the probe 26, in conjunction with an operation of the movable handle 272.

In the abovementioned first to sixth embodiments, the description has been given as to the example where the jaw 64 as the end effector is operated via the drive pipe 74 by the operation of the movable handle 94 to the fixed handle 92. In this embodiment, the acting section 274 as the end effector can directly be operated by the operation of the movable handle 272 to the fixed handle 92.

As shown in FIG. 16, the turning fulcrum 134 of the movable handle 272 is coupled with the support section 136 by a movable arm 160. A longitudinal axis (an extended axis defined by the turning fulcrum 134 and the support section 136) L is defined toward the support section 136 from a turning pin 142 that supports the movable handle 94 to allow its turning movement. The longitudinal axis L is present on the turning plane S1. A coupling section 166 has a turning shaft 168 that is orthogonal to the turning fulcrum 134 and the turning pin 142 and arranged along the longitudinal axis L. Thus, the coupling section 166 can turn the support section 136 in a periaxial direction of the longitudinal axis L. That is, a second arm 164 can turn in the periaxial direction of the longitudinal axis L to a first arm 162 by the turning shaft 168.

A finger hook section (an annular portion) 94c in which fingers except a thumb can be put is formed in the support section 136 of the movable handle 272. In the handle unit 22 according to this embodiment, a finger hook section 92b of the fixed handle 92 is caught with the fingers except the thumb and the finger hook section 94c of the movable handle 272 is caught with the thumb and supported. It is to be noted that a discoid plane (a virtual plane) S11 (see FIG. 7B) is defined on the turning plane 81 to the finger hook section 94c of the movable handle 94 by an edge portion of the finger hook section 94c in a neutral state that the support section 136 does not turn to an acting section 132.

Therefore, the coupling section 166 can be operated in the periaxial direction of the longitudinal axis L so that the discoid plane 811 of the finger hook section 94c of the movable handle 94 deviates from the turning plane S1, thereby suppressing and alleviating a burden on the finger put in the finger hook section 94c of the movable handle 94. Further, according to the surgical device 12 of this embodiment, at the time of treating a biological tissue while appropriately moving the handle unit 22, the handle unit can be moved without moving a position of the acting section 274 as the end effector as much as possible. Therefore, at the time of operating the movable handle 272, for example, when the handle unit 22 is inclined by the user's operation, the support section 136 can be operated in a direction to deviate from the turning plane S1 in the coupling section 166. Consequently, the acting section 274 as the end effector can be easily held at a fixed position irrespective of the inclination of the handle unit 22.

It is to be noted that, as shown in FIG. 16, at a tip of the sheath 28a, there may be disposed a cover (a probe protecting member) 28b that covers a proximal portion of the treatment section 54 of the probe 26 which is close to the probe main body 52. The cover 28b is extended from the tip of the sheath 28a further toward a distal side (the distal side of the treatment section 54 of the probe 26). The cover 28b is arranged on a side opposite to the acting section 274.

In this embodiment, the description has been given as to the example where the surgical device 12 has the probe 26 that transmits ultrasonic vibration, but it is also preferable to simply arrange a fixed jaw in place of the probe 26.

An eighth embodiment will now be described with reference to FIG. 17. This embodiment is a modification of the first to seventh embodiments, especially a modification of the seventh embodiment, and like reference numerals denote the same members or members having the same functions as the members described in the first to seventh embodiments as much as possible to omit a detailed description.

Figure 17:
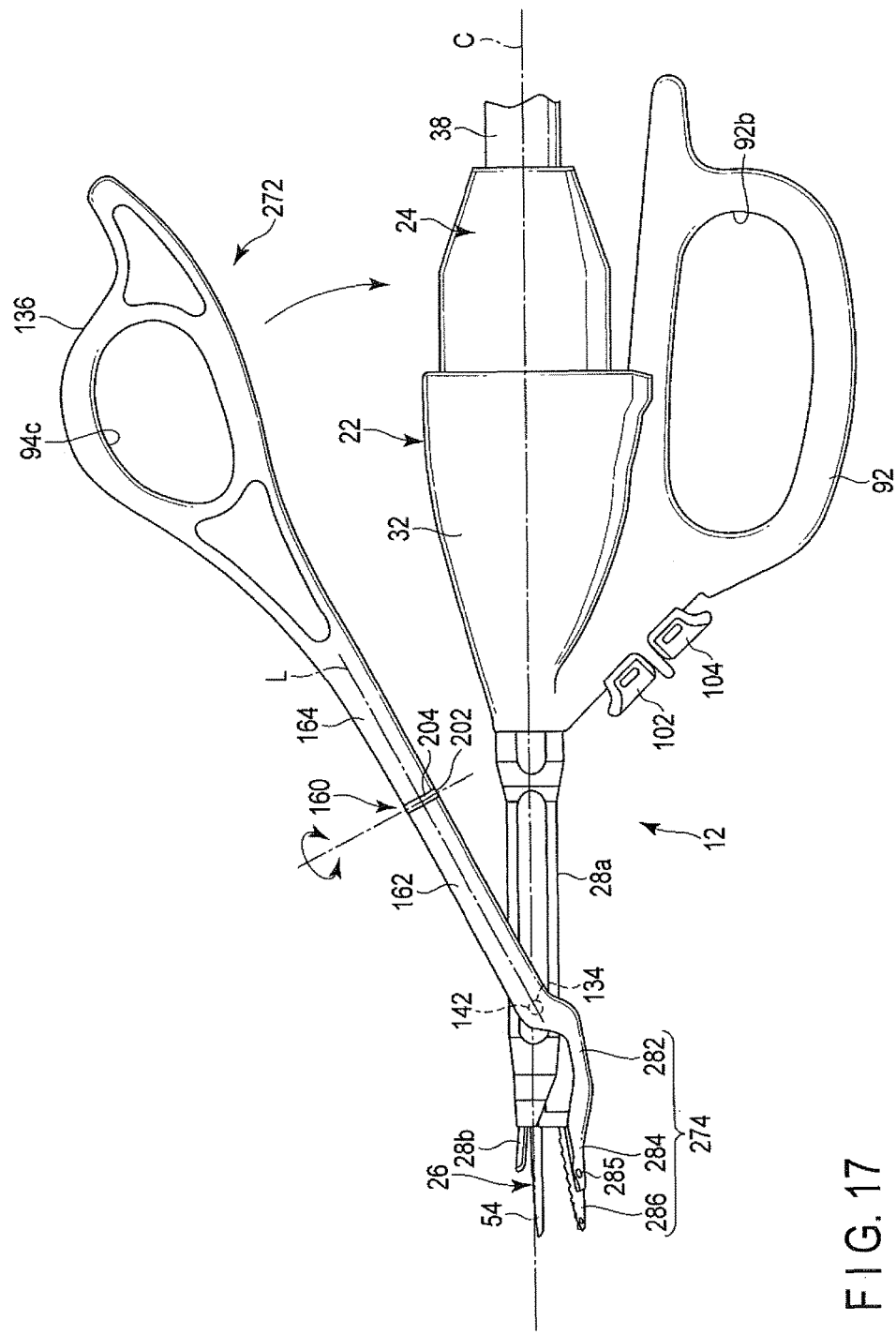
FIG. 17 is a schematic view showing a surgical device according to an eighth embodiment.

As shown in FIG. 17, a movable arm 160 of a movable handle 272 according to this embodiment includes a first arm (a top handle) 162 that moves closer to a turning fulcrum 134, i.e., a turning pin 142, a second arm (a bottom handle) 164 that moves closer to the support section 136, and a coupling section (a second coupling section) 202 that couples the first arm 162 with the second arm 164.

The coupling section 202 has a turning shaft 204 that is orthogonal to the turning fulcrum 134 and the turning pin 142 and is also orthogonal to a longitudinal axis L. Thus, the coupling section 202 can turn the support section 136 in a periaxial direction orthogonal to the longitudinal axis L. That is, the second arm 164 can turn to the first arm 162 in the periaxial direction orthogonal to the longitudinal axis L by the turning shaft 204. Therefore, the coupling section 202 can operate so that the support section 136 moves on a turning plane S2 (see FIG. 9B) orthogonal to a turning plane S1 formed when the movable handle 94 moves to a fixed handle 92, thereby suppressing and alleviating a burden on a finger put in a finger hook section 94c of the movable handle 272. Further, according to a surgical device 12 of this embodiment, at the time of treating a biological tissue while appropriately moving a handle unit 22, the handle unit can be moved without moving a position of an acting section 274 as an end effector as much as possible. Therefore, at the time of operating the movable handle 272, for example, when the handle unit 22 is inclined by a user's operation, the support section 136 can be operated in a direction to deviate from the turning plane S1 in the coupling section 202. Consequently, the acting section 274 as the end effector can be easily held at a fixed position irrespective of the inclination of the handle unit 22.

It is to be noted that, in the seventh embodiment, the description has been given as to the example where the support section 136 turns to the turning fulcrum 134 in the periaxial direction of the longitudinal axis L, and in the eighth embodiment, the description has been given as to the example where the support section 136 turns to the turning fulcrum 134 in a periaxial direction to deviate from the longitudinal axis L. It is also preferable that, in the movable handle 272, both of two coupling sections 212 and 214 are arranged as described in the third embodiment shown in FIG. 10A and FIG. 10B. In addition, it is also preferable that both of two coupling sections 362 and 364 are arranged as described in a later-described ninth embodiment shown in FIG. 18.

The ninth embodiment will now be described with reference to FIG. 18. This embodiment is a modification of the first to eighth embodiments, and like reference numerals denote the same members or members having the same functions as the members described in the first to eighth embodiments as much as possible to omit a detailed description. In this embodiment, the handle unit 22 described in the fourth embodiment (see FIG. 11) is modified.

Figure 18:
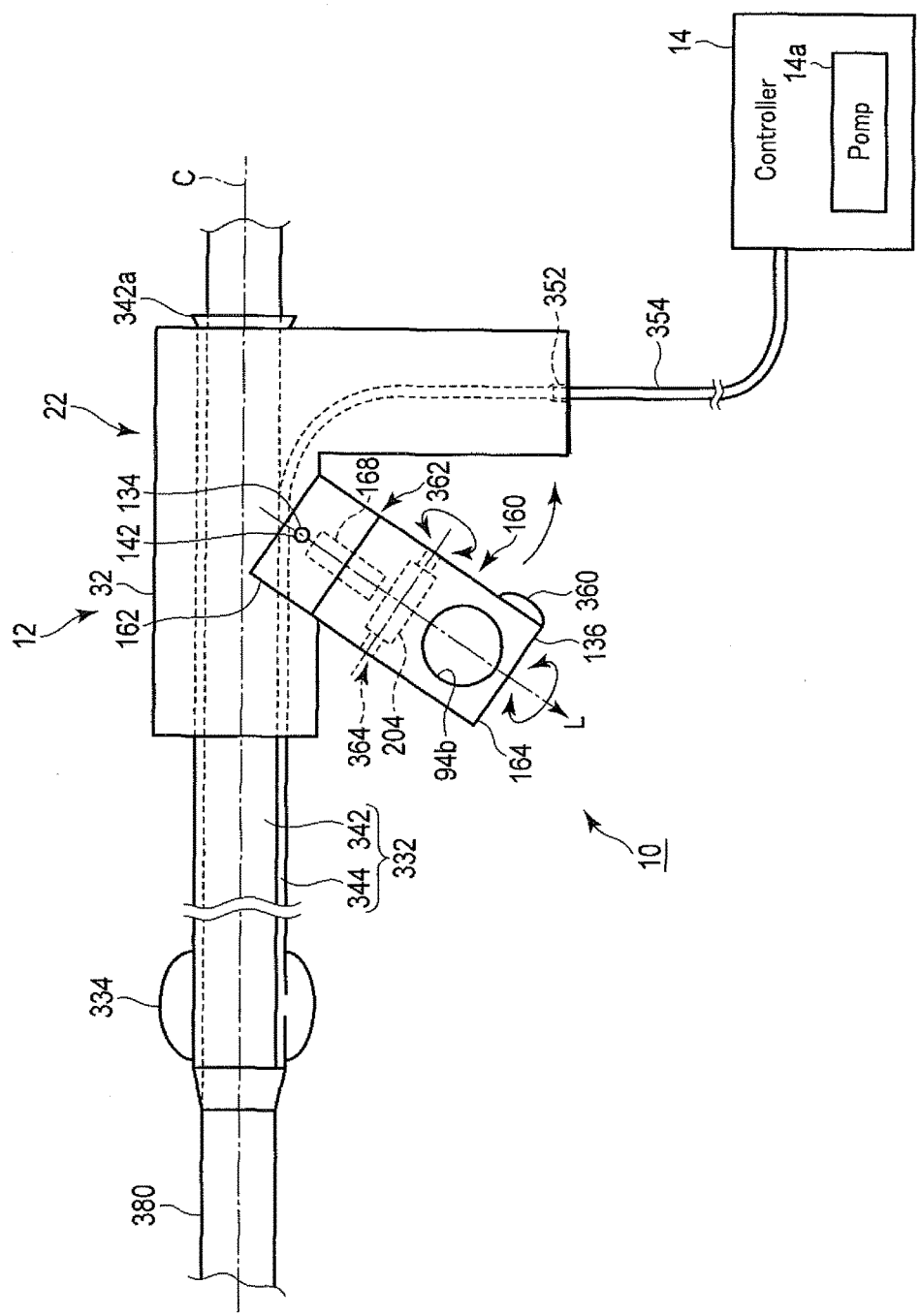
FIG. 18 is a schematic view showing a surgical system according to a ninth embodiment.

As shown in FIG. 18, a surgical system 10 according to this embodiment includes a surgical device 12 and a controller 14 that controls this device 12. In this embodiment, a description will be given on the assumption that the surgical device 12 is a catheter 324 capable of expanding and contracting a later-described balloon 334. That is, in this embodiment, the ultrasonic transducer unit 24, the probe 26 and the sheath unit 28 described in the first to sixth embodiments are not required, but instead, the catheter 324 is disposed in a handle unit 22. It is to be noted that the controller 14 has a pump 14a that expands and contracts the balloon.

The surgical device 12 includes the handle unit 22 and the catheter 324. The catheter 324 has a tubular main body 332, and the balloon 334 as an end effector disposed on an outer peripheral surface of a distal portion of the tubular main body 332. The tubular main body 332 has a tube path 342 into which a treatment tool 380 such as a guide wire is inserted, and a flow path 344 to expand or contract the balloon 334. The flow path 344 communicates with the balloon 334.

Further, the tube path 342 is fixed to the handle unit 22 along a center axis C. The handle unit 22 has an opening 342a of the tube path 342 at a rear end thereof. The flow path 344 is branched from the tubular main body 332 in, e.g., a handle main body 32 to be connected to a mouthpiece 352 arranged at a lower end of a fixed handle 92. The mouthpiece 352 is connected to the pump 14a in the controller 14 by a hose 354.

At a lower end of a movable handle 94, a switch 360 is disposed, e.g., at a position to be confronted with a front surface of the fixed handle 92. The switch 360 is electrically connected to the controller 14. When the movable handle 94 is moved closer to the fixed handle 92 and the switch 360 is pressed by the front surface of the fixed handle 92, the controller 14 controls the pump 14a to feed a gas such as air to the balloon 334 through the hose 354, the mouthpiece 352 and the flow path 344 of the catheter 324 in this order. Further, the balloon 334 is expanded. The controller 14 automatically stops an operation of the pump 14a when a pressure in the hose 354 reaches a predetermined value. On the other hand, when the movable handle 94 is moved away from the fixed handle 92 to release the switch 360 pressed by the front surface of the fixed handle 92, the controller 14 controls the pump 14a to suck a gas such as air in the balloon 334, thereby contracting the balloon 334.

A movable arm 160 of the movable handle 94 according to this embodiment includes a first arm (a top handle) 162 that moves closer to a turning fulcrum 134, i.e., a turning pin 142, a second arm (a bottom handle) 164 that moves closer to a support section 136, and coupling sections 362 and 364 that couple the first arm 162 with the second arm 164. That is, the movable handle 94 has the two coupling sections 362 and 364. Here, the coupling section 362 has the same configuration as the coupling section 166 (see FIG. 7A and FIG. 7B) described in the first embodiment, and the coupling section 364 has the same configuration as the coupling section 202 (see FIG. 9A and FIG. 9B) described in the second embodiment. That is, in one coupling section (a second coupling section) 362, the second arm 164 can be turned to the first arm 162 in a periaxial direction along a longitudinal axis L by a turning shaft 168. In the other coupling section (a third coupling section) 364, the second arm 164 can be turned to the first arm 162 in a periaxial direction orthogonal to the longitudinal axis L by a turning shaft 204.

Therefore, according to a surgical device 12 of this embodiment, the support section 136 can be turned to an acting section 132 in a predetermined range around the longitudinal axis L by the turning shaft 168 (see FIG. 7A and FIG. 7B), and in a predetermined range around an axis orthogonal to the longitudinal axis L by the turning shaft 204 (see FIG. 9A and FIG. 9B). Thus, according to the movable handle 94 of this embodiment, it is possible to further increase a degree of freedom in a moving range of the movable handle 94 of the handle unit 22 described in the first embodiment and the second embodiment.

In the surgical device 12 of the surgical system 10 of the present embodiment, the support section 136 (the second arm 164) of the movable handle 94 can be turned in periaxial directions of the turning shafts 168 and 204 in accordance with a direction of the handle unit 22 grasped by a user. That is, the support section 136 of the movable handle 94 can be turned to the acting section 132, and hence at the time of moving the handle unit 22 and maintaining a moved state, a burden received from the movable handle 94 by the user can be suppressed and alleviated.

In a certain case, the user, i.e., a surgeon gives a treatment with the treatment tool 380 inserted through the tube path 342 while enlarging an end effector (the balloon 334 in this embodiment) at a given position and while directing a palm or a back of a hand upward to change a direction of the entire handle unit 22 to various positions. It imposes a burden on the user's hand to move the entire handle unit 22 while maintaining the end effector at the given position and disposing the movable handle 94 close to the fixed handle 92. That is, at the time of giving the treatment to the same treatment target at various angles with the use of the end effector, a considerable burden is imposed on the user's hand with movement of the entire handle, and hence it is a difficult operation. According to the surgical device 12 of this embodiment, as different from, e.g., a device in which a direction of the fixed handle 92 is adjustable, as disclosed in International Publication No. WO 2005/112795, an angle of the movable handle 94 can be adjusted in accordance with a burden on the fingers except a thumb put in a finger hook section 94b. Thus, in a case of operating the movable handle 94 and in a case of operating the movable handle 94 and then maintaining this state, the burden imposed on the user's hand can further be alleviated and suppressed. Thus, in the surgical device 12 according to this embodiment, at the time of operating the movable handle 94 and at the time of operating the movable handle 94 and then maintaining this state, the burden is hardly imposed on the user, and an excellent operational feeling can be obtained. Therefore, the handle unit 22 can easily be moved without moving a position of the balloon 334, i.e., a position of the end effector as much as possible, and the state can readily be maintained after moving the handle unit 22.

In this embodiment, the description has been given as to the example where the turning shaft 168 along the longitudinal axis L is arranged on a side close to the turning fulcrum 134 along the longitudinal axis L and the turning shaft 204 orthogonal to the longitudinal axis L is arranged on a side away from the turning fulcrum 134. As described in the first and second embodiments, arranging one of the turning shafts 168 and 204 alone is also preferable.

In the abovementioned first to sixth embodiments, the jaw 64 has been described as the end effector; in the seventh and eighth embodiments, the acting section 274 has been described as the end effector; and in the ninth embodiment, the balloon 334 has been described as the end effector. The end effector is not restricted to these examples, and various members are usable as long as various treatments are given by moving the movable handle 94 or 272 to the fixed handle 92 to operate the end effector.

Hitherto, several embodiments have specifically been described with reference to the drawings, but this invention is not limited to the abovementioned embodiments, and includes all implementations carried out without departing from the gist of the present invention.

[Reference Embodiments]

For example, International Publication No. WO 2009/046234 discloses a treatment tool having a handle unit. Two pressing switches are arranged on a front surface of this handle unit of the treatment tool.

The handle unit only having the two pressing switches is usually switchable only between two modes. For example, it is possible to switch to three modes by pressing one of the two pressing switches twice in a short time (double click) or pressing the two pressing switches at the same time. It is considered that a desired operation cannot be performed depending on a pressing timing to double click one of the two pressing switches or a pressing timing of the two pressing switches. In addition, when the handle unit has such pressing switches, the operation of the handle unit is disadvantageously complicated.

In this reference embodiment, there is provided an easily operable handle unit having at least three switches.

A first reference embodiment will now be described with reference to FIG. 19 to FIG. 22C. It is to be noted that descriptions of the same members as the members described in the abovementioned first to ninth embodiments are omitted as much as possible.

Figure 19:
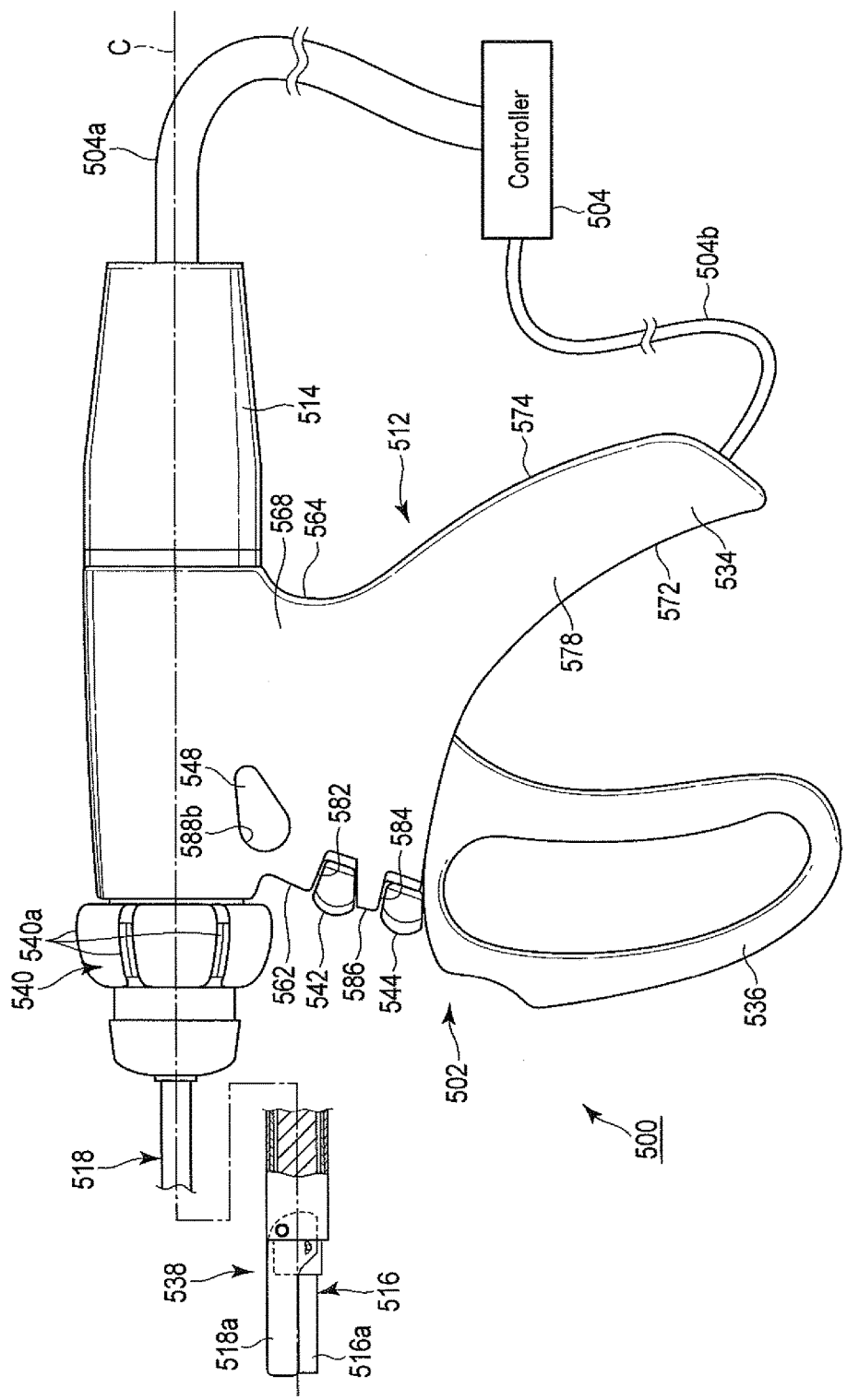
FIG. 19 is a schematic view showing a surgical system having a handle unit showing a left side surface according to a first reference embodiment.

As shown in FIG. 19, a surgical system 500 according to the first reference embodiment includes a surgical device 502 and a controller 504 that controls this device 502. It is to be noted that, in the first reference embodiment, a description will be given on the assumption that the surgical device 502 is an energy treatment tool using high frequency energy and ultrasonic vibration energy.

The surgical device 502 has a handle unit 512, an ultrasonic transducer unit 514, a probe 516 (see FIG. 3), and a sheath unit 518. The handle unit 512 has a center axis C. For example, the handle unit 512 is coupled to the transducer unit 514, the probe 516 and the sheath unit 518 on the center axis C.

It is to be noted that the ultrasonic transducer unit 514 is electrically connected to the controller 504 by a first cord 504a, and later-described and non-illustrated high frequency electrodes are electrically connected to the controller 504 by a second cord 504b that is attachable to or detachable from a later-described fixed handle 534. The first cord 504a and/or the second cord 504b is usable in electrically connecting each of later-described first to fourth switches 542, 544, 546 and 548 to the controller 504.

As shown in FIG. 20, the handle unit 512 according to the first reference embodiment is substantially shaped in the form of a pistol. The handle unit 512 is substantially symmetrically formed so that both right-handed and left-handed users can obtain the same operational feeling.

The handle unit 512 has a handle body 532, the fixed handle (a grip) 534 disposed in the body 532, a movable handle (a trigger) 536 supported by the body 532, a rotary knob 540 that allows an end effector 538 (see FIG. 19) to rotate, and the first to fourth switches 542, 544, 546 and 548 disposed in the body 532. It is to be noted that, in this reference embodiment, a description will be given on the assumption that each of the first to fourth switches 542, 544, 546 and 548 is a pressing switch that is changed from OFF to ON when the switch is pressed with a fingertip, and changed from ON to OFF when the pressed switch is released.

In the handle unit 512, the movable handle 536 is arranged on a front side along the center axis C and the fixed handle 534 is disposed on a rear side along the same. Thus, when the movable handle 536 is moved, i.e., turned toward the fixed handle 534 on the rear side, the end effector 538 can be operated.

The first to fourth switches 542, 544, 546 and 548 are electrically connected to the controller 504 shown in FIG. 19. Later-described various functions are appropriately assigned to the respective switches 542, 544, 546 and 548 by the controller 504. Thus, when each of the switches 542, 544, 546 and 548 is pressed, a signal is transmitted to the controller 504 from each of the switches 542, 544, 546 and 548, and the controller 504 allows the end effector 538 to exert various functions as described later on the basis of the functions assigned to the switches 542, 544, 546 and 548.

As the end effector 538, the jaw 64 may be used as described in the abovementioned first to sixth embodiments, the acting section 274 may be used as described in the seventh and eighth embodiments, and the balloon 334 may be used as described in the ninth embodiment. Furthermore, the end effector is not restricted to these examples, and various members are usable as long as various treatments can be given by moving the movable handle 536 to the fixed handle 534 to operate the end effector 538.

In this reference embodiment, the end effector 538 has, e.g., a treatment section 516a of the probe 516, and a jaw 518a that can come in contact with and move away from the treatment section 516a and has a non-illustrated high frequency electrode arranged on a grasping surface thereof. The treatment section 516a of the probe 516 is used not only to apply ultrasonic vibration to a biological tissue, but also to prepare a closed loop through the biological tissue of a treatment target grasped between the treatment section and the high frequency electrode of the grasping surface of the jaw 518a, thereby treating the target with high frequency energy (heat energy). That is, the treatment section 516a of the probe 516 and the high frequency electrode of the grasping surface of the jaw 518a are used as bipolar electrodes. On the other hand, the high frequency electrode of the grasping surface of the jaw 518a or the treatment section 516a of the probe 516 that is the high frequency electrode is used to prepare the closed loop between the electrode and a counter electrode plate (not shown) to be attached to a human body or the like, thereby treating the treatment target with the high frequency energy (the heat energy). That is, the treatment section 516a of the probe 516 and the high frequency electrode of the grasping surface of the jaw 518a in this case are used as monopolar electrodes.

As shown in FIG. 20, the body 532 has a tubular section 552 in which the center axis C is defined, and an extended section 554 formed integrally with the tubular section 552. A length of the tubular section 552 in an axial direction along the center axis C is appropriately settable. The extended section 554 is extended away from the center axis C. The first to fourth switches 542, 544, 546 and 548 are arranged in the extended section 554. The fixed handle 534 is formed integrally with the extended section 554. It is to be noted that the extended section 554 and the fixed handle 534 are arranged in order away from the center axis C.

The movable handle 536 movably supported by the body 532 moves closer to or away from the fixed handle 534 substantially in parallel with the center axis C. Usually, the movable handle 536 is separated from the fixed handle 534 due to an urging force of an elastic body such as a non-illustrated spring supported between the fixed handle 534 and the movable handle 536. In the movable handle 536, there is formed a finger hook section (an annular portion) 536a in which fingers except a thumb are put. It is to be noted that a front surface 536b of the movable handle 536 is present on a front side from a front surface 562 of the extended section 554 in this reference embodiment. An upper surface 536c of the movable handle 536 is disposed away from a lower surface of the second switch 544 via a slight space.

At a tip of the tubular section 552 of the body 532, the rotary knob 540 rotatable in a periaxial direction of the center axis C is disposed. The rotary knob 540 can turn the end effector 538 in the periaxial direction of the center axis C by the mechanism (see FIG. 5 to FIG. 6B) described in the first embodiment. In an outer peripheral surface of the rotary knob 540, ribs 540a are formed. A space between the ribs 540a is, e.g., suitably approximately a width of an index finger. Thus, the outermost periphery of the rib 540a is held with a finger sphere of a fingertip of the index finger, or the fingertip of the index finger is interposed between the adjacent ribs 540a, so that the rotary knob 540 can be rotated in the periaxial direction of the center axis C.

The extended section 554 of the body 532 has the front surface 562, a rear surface 564 and a pair of side surfaces 566 and 568. A boundary between the front surface 562 of the extended section 554 and each of the right side surface 566 and the left side surface 568 is formed in a smoothly curved surface. A boundary between the rear surface 564 of the extended section 554 and each of the right side surface 566 and the left side surface 568 is formed in a smoothly curved surface. The front surface 562 of the extended section 554 is formed in a substantially circularly curved surface by directing a normal in a direction closer to the center axis C. In FIG. 19 and FIG. 20, a region of the front surface 562 of the extended section 554 which is close to the tubular section 552 is present on a proximal side from the tip of the tubular section 552, but may be present at the same position as the tip of the tubular section. The rear surface 564 of the extended section 554 is formed in a smoothly curved surface 564a that is convex toward a distal side of the center axis C, to a proximal end of the tubular section 552.

The fixed handle 534 has a front surface 572, a rear surface 574 and a pair of side surfaces 576 and 578. The front surface 572 of the fixed handle 534 is formed in a circularly curved surface by directing a normal in a direction away from the center axis C. A boundary between the rear surface 574 of the fixed handle 534 and each of the right side surface 576 and the left side surface 578 is formed in a smoothly curved surface. The rear surface 574 of the fixed handle 534 is formed in a substantially circularly curved surface by directing a normal in a direction closer to the center axis C. The rear surface 574 of the fixed handle 534 is extended toward the proximal side of the center axis C as the rear surface is curved away from the center axis C.

The rear surface 564 of the extended section 554 is formed continuously with the rear surface 574 of the fixed handle 534. A base between the thumb and the index finger of a user's hand H, i.e., a web of the base between the thumb and the index finger is put on the curved surface 564a of the rear surface 564 of the extended section 554. Thus, the extended section 554 can be held in the state that the web between the thumb and the index finger is put on the curved surface 564a of the rear surface 564 of the extended section 554. Further, the rear surface 574 and the pair of side surfaces 576 and 578 of the fixed handle 534 are held between a thenar and a little finger sphere of a palm of the same hand H of the user.

It is to be noted that regions on which the web between the thumb and the index finger is put, i.e., the rear surface 564 of the extended section 554 and the rear surface 574 of the fixed handle 534 are formed in a curved surface that is continuous from the proximal end of the tubular section 552. In this reference embodiment, the region that is away from the tubular section 552 in the rear surface 564 of the extended section 554, or the rear surface 574 of the fixed handle 534 is present on the proximal side further from the proximal end of the tubular section 552. The second cord 504b shown in FIG. 19 is arranged in a region of the fixed handle 534 which is distant to the center axis C.

As shown in FIG. 19 and FIG. 20, in the front surface 562 of the extended section 554, there are formed a first switch disposing section 582 where the first switch 542 is disposed, a second switch disposing section 584 where the second switch 544 is disposed, and a partition 586 via which the first switch 542 is separated from the second switch 544. Due to the partition 586, the first switch 542 and the second switch 544 can clearly be distinguished with the finger sphere of the fingertip of the index finger. The first switch disposing section 582 and the second switch disposing section 584 are formed to be concaved to the front surface 562 of the extended section 554. The first switch disposing section 582 is closer to the center axis C than the second switch disposing section 584. That is, in the front surface 562 of the extended section 554, there are arranged the first switch 542 disposed closer to the center axis C and the second switch 544 disposed farther to the center axis C than the first switch 542. A length between a central portion of the surface of the first switch 542 on a front side and a central portion of the surface of the second switch 544 on the front side is about 13 mm.

It is to be noted that functions to be assigned to the first and second switches 542 and 544 are set as pressing switches that allow the end effector 538 to exert the respective functions when the first and second switches 542 and 544 are pressed, respectively, by the controller 504.

As shown in FIG. 20, in the right side surface 566 of the extended section 554, there is formed a third switch disposing section 588a where the third switch 546 is disposed. As shown in FIG. 19, in the left side surface 568 of the extended section 554, there is formed a fourth switch disposing section 588b where the fourth switch 548 is disposed. Consequently, the third switch 546 is present in the right side surface 566 of the extended section 554 as shown in FIG. 20, and the fourth switch 548 is present in the left side surface 568 of the extended section 554 as shown in FIG. 19. It is to be noted that the third and fourth switches 546 and 548 are preferably present at symmetric positions so that both the left-handed and right-handed users can obtain the same operational feeling.

As shown in FIG. 21A, the third switch disposing section 588a has a receiving portion 592 in which the third switch 546 is received. An edge portion 546a of an outer surface of the third switch 546 is formed on the same plane as the right side surface 566. That is, the third switch disposing section 588a is formed so that the outer surface of the third switch 546 is the same surface as the right side surface 566. Consequently, for example, when the fingers are moved from a state shown in FIG. 22A to a state shown in FIG. 22C, a finger such as the index finger can be prevented from being caught in the edge portion of the third switch 546.

Therefore, for example, when the palm of the right hand H abuts on the third switch 546 in a state where the handle unit 512 is held by the right hand H, the third switch 546 can be prevented from being pressed with the palm of the right hand H. Consequently, a wrong operation of the third switch 546 is prevented.

As shown in FIG. 21B, the third switch disposing section 588a also preferably has a receiving portion 594a in which the third switch 546 is received, and an annular concave portion 594b formed continuously with the receiving portion 594a in the right side surface 566. Further, the outer surface of the third switch 546 protrudes outwardly to the annular concave portion 594b. On the other hand, the outer surface of the third switch 546 is formed to be the same surface as the outer surface of the right side surface 566. Consequently, the edge portion 546a of the third switch 546 can be found with a sense of touch of the finger by moving the finger without visually recognizing the third switch 546.

In addition, the annular concave portion 594b and the edge portion 546a of the third switch 546 on an inner side of the concave portion are preferably formed in such a size that the third switch 546 can be pressed with the finger sphere of the fingertip but the third switch 546 cannot be pressed at a position of a first joint of the finger to a wrist. Therefore, even when the palm of the right hand H abuts on the third switch 546 in a state where the handle unit 512 is held by the right hand H, the third switch 546 is prevented from being pressed. Consequently, the wrong operation of the third switch 546 is prevented.

It is to be noted that, here, the description has been given as to the arrangement of the third switch 546 to the right side surface 566, but this preferably also applies to the arrangement of the fourth switch 548 to the left side surface 568.

In the rear surface 564 of the extended section 554 of the body 532 and the rear surface 574 of the fixed handle 534, a position where the web between the thumb and the index finger of the user's hand H is put is an origin O. When a length La from the origin O to the third switch 546 is compared with a length Lb from the third switch 546 to the rotary knob 540, it is preferable that the lengths are the same or that the length from the origin O to the third switch 546 is longer (La≥Lb). It is to be noted that, in this reference embodiment, a length L3 (La+Lb) from the origin O to the rotary knob 540 is defined on the basis of a central position between the distal end and the proximal end of the rotary knob 540 in a direction along the center axis C.

It is to be noted that functions to be assigned to the third and fourth switches 546 and 548 are set as pressing switches that allow the end effector 538 to exert the same function when each of the third and fourth switches 546 and 548 is pressed, by the controller 504. Alternatively, the functions to be assigned to the third and fourth switches 546 and 548 are set as the pressing switches that allow the end effector 538 to exert different functions when the third and fourth switches 546 and 548 are pressed, respectively, by the controller 504. In the latter case, when the handle unit 512 is held by the right hand H, the third switch 546 is operated with the index finger of the right hand H, and the fourth switch 548 is operated with the left hand. Similarly, when the handle unit 512 is held by the left hand, the fourth switch 548 is operated with the index finger of the left hand, and the third switch 546 is operated with the right hand.

It is to be noted that a length L1 from the origin O to the central portion of the front surface of the first switch 542 is about 62 mm, a length from the origin O to the central portion of the front surface of the second switch 544 is about 66 mm, and the length L3 (La≥Lb) from the origin O to the central position of the rotary knob 540 is about 75 mm. In addition, the length La from the origin O to the third switch 546 is about 43 mm. In particular, the third switch 546 is preferably arranged on a fingertip side from a second joint of the index finger in a state where the rotary knob 540 is supported with the finger sphere of the fingertip of the index finger.

In the first reference embodiment, a position of the central portion of the surface of the first switch 542 on the side of the front surface 562 of the extended section 554 is tilted upwardly (on the side closer to the center axis C) as much as about 4° to an axis passing the origin O in parallel with the center axis C. A position of the central portion of the surface of the second switch 544 on the side of the front surface 562 of the extended section 554 is tilted downwardly (on the side away from the center axis C) as much as about 7° to the axis passing the origin O in parallel with the center axis C. Consequently, an angle between the central portion of the surface of the first switch 542 and the central portion of the surface of the second switch 544 to the origin O is about 11°. In addition, the central position of the rotary knob 540 is inclined upwardly (on the side closer to the center axis C) as much as about 27° to the axis passing the origin O in parallel with the center axis C. Consequently, an angle between the central position of the rotary knob 540 and the central portion of the surface of the second switch 544 to the origin O is about 35°. In addition, a length between the center axis C of the rotary knob 540 and the central portion of the surface of the second switch 544 is about 43 mm.

Figure 22B:
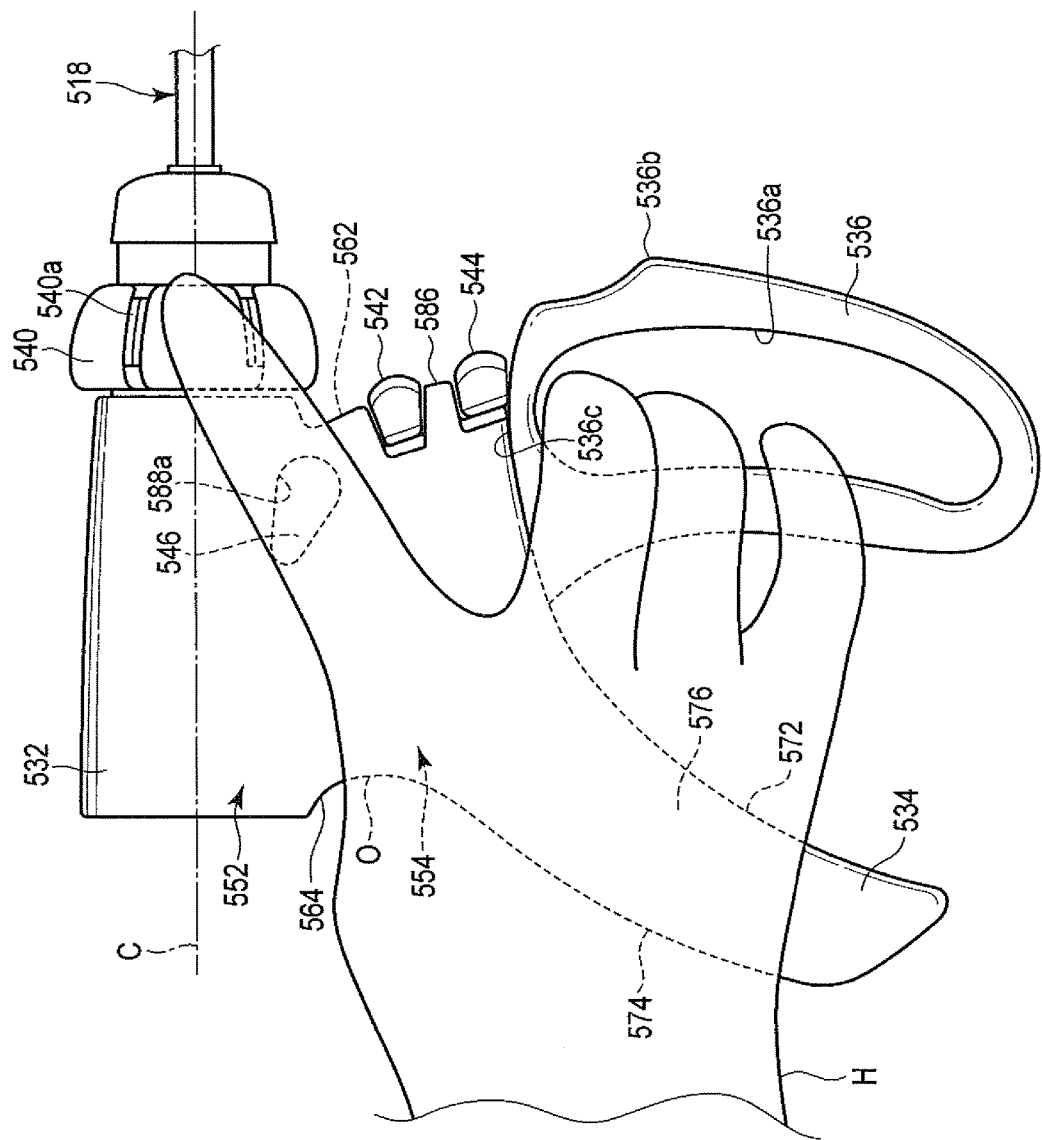
FIG. 22B is a schematic right side view showing a state that the finger sphere of the fingertip of the index finger is arranged on a rotary knob while holding the handle unit of the surgical system according to the first reference embodiment by the right hand and hiding the third switch with the index finger.

Consequently, as shown in FIG. 22A and FIG. 22B, the rotary knob 540 and the first to third switches 542, 544 and 546 are arranged, respectively, at positions reached by the finger sphere of the fingertip of the index finger of the user's hand H in a state where the web between the thumb and the index finger of the user's right hand H is put on the rear surface 564 of the extended section 554 of the body 532 and the rear surface 574 of the fixed handle 534, when the handle unit 512 is held by the right hand H. Although not shown, the rotary knob 540, the first switch 542, the second switch 544 and the fourth switch 548 are similarly arranged, respectively, at positions reached by the finger sphere of the fingertip of the index finger of the user's hand in a state where the web between the thumb and the index finger of the user's left hand is put on the rear surface 564 of the extended section 554 of the body 532 and the rear surface 574 of the fixed handle 534, when the handle unit 512 is held by the left hand.

Here, (L3−La)/La is preferably one or more. That is, the third switch 546 is present at a position closer to the rotary knob 540 than the origin O. Consequently, a moving amount of the index finger from the rotary knob 540 to the third switch 546, from the first switch 542 to the third switch 546 or from the second switch 544 to the third switch 546 can be made smaller as compared with a case where the third switch is present at a position closer to the origin O.

In addition, it can be considered that, with such angles and lengths, a moving range of the index finger is ergonomically natural when the finger sphere of the fingertip of the index finger is moved between the central position of the rotary knob 540 and the central portion of the surface of the second switch 544 in the state where the web between the thumb and the index finger is put on the rear surface 564 of the extended section 554. That is, it can be considered that, needless to say, it is natural to move the finger sphere of the fingertip of the index finger between the first switch 542 and the second switch 544 and between the rotary knob 540 and the first switch 542. Furthermore, in a state where the index finger is extended to hold the rotary knob 540 with the finger sphere of the fingertip of the index finger, the third switch 546 is present at a position to be hidden with the index finger. On the other hand, when the index finger is bent at the joint to detach the finger sphere of the fingertip of the index finger from the rotary knob 540, the third switch 546 can be pressed.

An operation of the surgical device 502 according to this reference embodiment will now be described.

As shown in FIG. 22A, the handle unit 512 is grasped by the right hand H. At this time, for example, the base between the thumb and the index finger of the user's hand H, i.e., the web of the base between the thumb and the index finger is put on the curved surface 564a of the rear surface 564 of the extended section 554. Furthermore, the rear surface 574 of the fixed handle 534 and the pair of side surfaces 576 and 578 of the extended section 554 are held to be sandwiched between the thenar and the little finger sphere of the palm of the right hand H. Consequently, the handle unit 512 can readily be held in a state where the web between the thumb and the index finger is put on the curved surface 564a of the rear surface 564 of the extended section 554. It is to be noted that the middle finger, ring finger and little finger of the right hand are put in the finger hook section 536a of the movable handle 536. Further, as shown in FIG. 22B, when the rotary knob 540 is rotated with the finger sphere of the index finger in the periaxial direction of the center axis C, the end effector 538 turns in the periaxial direction of the center axis C.

When the energy is applied to the biological tissue of the treatment target, as shown in FIG. 22A, the first switch 542 or the second switch 544 is caught and pressed with the finger sphere of the index finger. For example, when the central portion of the surface of the first switch 542 is pressed with the finger sphere of the index finger, the biological tissue of the treatment target, e.g., a blood vessel can be incised by the ultrasonic energy while coagulating the biological tissue of the treatment target, e.g., the blood vessel by bipolar energy. When the central portion of the surface of the second switch 544 is pressed with the finger sphere of the index finger, the biological tissue of the treatment target, e.g., the blood vessel can be sealed or bleeding can be stopped by the high frequency energy.

Figure 22C:
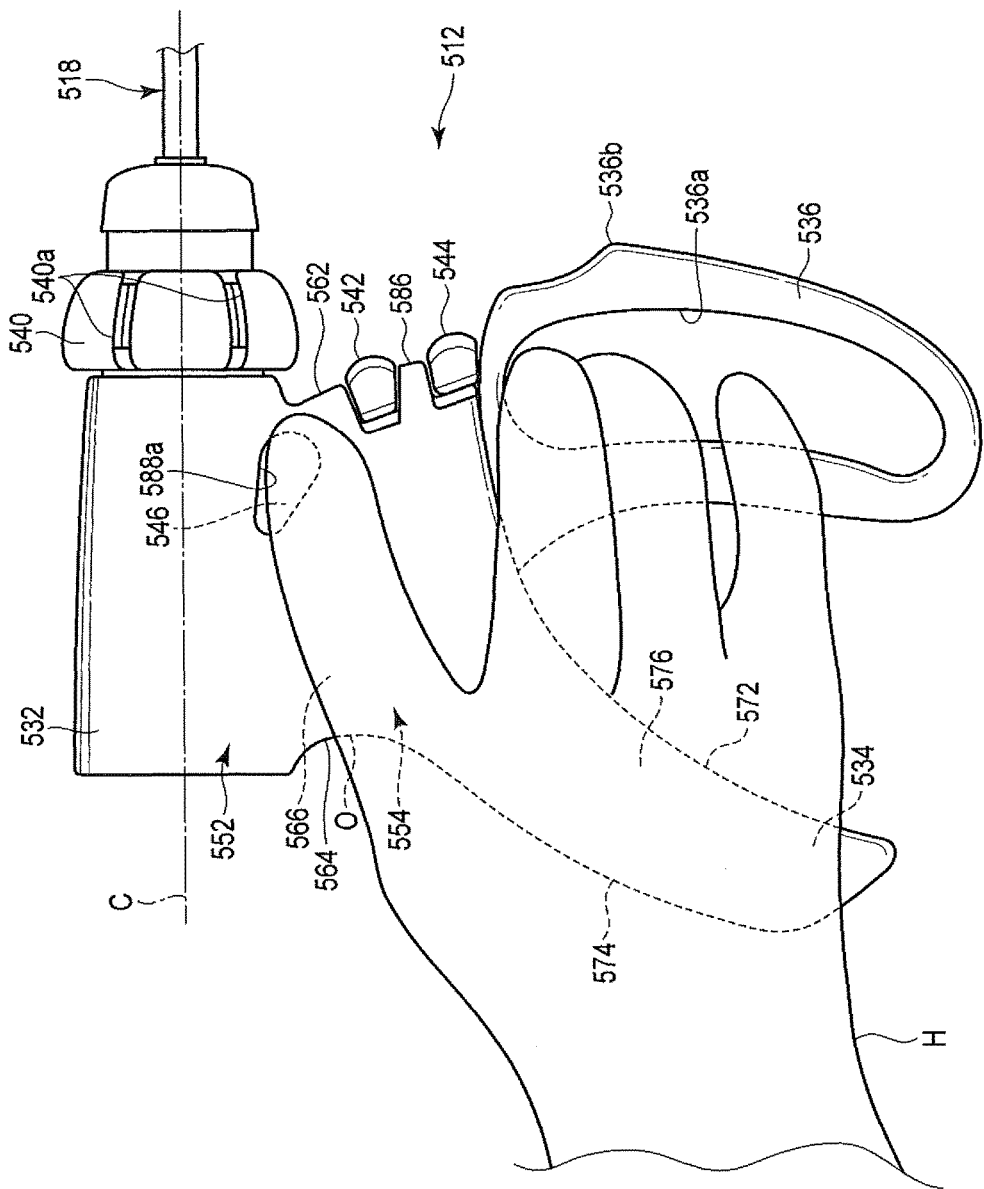
FIG. 22C is a schematic right side view showing a state that the finger sphere of the fingertip of the index finger is arranged on the third switch by bending the index finger at a joint to the state shown in FIG. 22B while holding the handle unit of the surgical system according to the first reference embodiment by the right hand.

As shown in FIG. 22C, by bending the index finger at the joint, the third switch 546 is caught and pressed with the finger sphere of the index finger. At this time, the third switch 546 is present in the moving range of the finger sphere of the index finger, and can accordingly be pressed easily. When the central portion of the surface of the third switch 546 is pressed with the finger sphere of the index finger, the bleeding of the biological tissue can be stopped or the tissue can be peeled by monopolar energy. A treatment such as the stopping of the bleeding by the monopolar energy can usually be given in a narrower range than in a treatment such as the stopping of the bleeding by the bipolar energy, due to a current density.

It is to be noted that, depending on the function assigned to the third switch 546, the biological tissue of the treatment target, e.g., the blood vessel can be incised by the ultrasonic energy, or the biological tissue of the treatment target can be incised by the ultrasonic energy while coagulating the biological tissue of the treatment target to stop the bleeding by the monopolar energy.

As shown in FIG. 21A and FIG. 21B, the third switch 546 is formed on the same surface as the right side surface 566. In addition, as to an operating force amount of the third switch 546, the switch cannot be pressed with the finger sphere between the first joint and the second joint of the index finger. Consequently, the third switch 546 is prevented from being wrongly operated. Therefore, the third switch 546 is prevented from being operated while operating the rotary knob 540 and the first and second switches 542 and 544.

The fourth switch 548 may be set for the left-handed user so that the same function as that of the third switch 546 is exerted. Additionally, the fourth switch 548 is not present at the position reached by the finger sphere of the index finger of the right hand H, but can be pressed with the left hand. Consequently, the fourth switch 548 may exert a function different from that of the third switch 546.

As described above, the first reference embodiment can be considered as follows.

L1, L2 and L3 are straight lines having different angles, respectively, to the origin O, and the third switch 546 is arranged on a straight line connecting the origin O to the central position of the rotary knob 540, between the origin O and the central position between the distal end and the proximal end of the rotary knob 540 in the direction along the center axis C. Consequently, the third switch 546 can easily be operated by changing a fingertip position of the index finger in a state where the handle unit 512 is grasped with the right hand H by the user. The third switch 546 is present in a triangle formed to the origin O by the central position of the operating knob 540 and the central portion of the surface of the second switch 544, and hence the index finger can ergonomically naturally be moved. In particular, the third switch 546 is present at a position closer to the rotary knob 540 than a midpoint between the origin O and the central position of the rotary knob 540, and hence the finger sphere of the fingertip can be disposed in the third switch 546 simply by slightly moving the index finger to the third switch 546.

It is to be noted that colors of the first to third switches 542, 544 and 546 are preferably different from one another to such an extent that the difference is distinguishable, and the third switch 546 and the fourth switch 548 preferably have the same color. The colors can appropriately be set. That is, for example, the first switch 542 is set to be purple, the second switch 544 is set to be blue, and the third and fourth switches 546 and 548 are set to be yellow.

In the surgical device 502 according to the first reference embodiment, the following treatments (1) to (5) can be given to the biological tissue by the end effector 538. To each of the first to third switches 542, 544 and 546, for example, one of the following treatments (1) to (5) is selected and set. The surgical device 502 can give the treatments: (1) the sealing or incision of the blood vessel by simultaneous output of the ultrasonic vibration energy and the bipolar energy (giving the treatment by ultrasonic vibration and outputting, from the end effector 538, energy to give a bipolar treatment); (2) the sealing or bleeding stopping of the blood vessel by the output of the bipolar energy (outputting, from the end effector 538, the energy to give the bipolar treatment); (3) pinpoint bleeding stopping or mucous membrane peeling by the output of the bipolar energy (outputting, from the end effector 538, the energy to give the bipolar treatment); (4) the incision of the biological tissue by the output of the ultrasonic vibration energy (outputting, from the end effector, the energy to give the ultrasonic vibration treatment); and (5) the pinpoint bleeding stopping, mucous membrane peeling, or inhibition of the biological tissue from adhering to the treatment section 516a of the probe 516, by the simultaneous output of the monopolar energy and the ultrasonic vibration energy (outputting, from the end effector 538, the energy to give the monopolar treatment or the ultrasonic vibration treatment). It is to be noted that the same function as that of the third switch 546 or the function different from those of the first to third switches 542, 544 and 546 can be set to the fourth switch 548.

In this reference embodiment, the description has been given on the assumption that the first to fourth switches 542, 544, 546 and 548 are the pressing switches that are pressed to allow the end effector 538 to exert the function. As each of the first and second switches 542 and 544, it is also preferable to use a slide switch or the like in which, for example, a neutral position (the center of the front surface 562 of the extended section 554) is set to an OFF-state and which is moved toward the left side surface 568 or the right side surface 566 to be changed to ON. At this time, when the first switch 542 is moved from the neutral position toward the left side surface 568 or the right side surface 566, the end effector 538 is preferably allowed to exert the same function. Similarly, when the second switch 544 is moved from the neutral position toward the left side surface 568 or the right side surface 566, the end effector 538 is preferably allowed to exert the same function. In addition, as each of the third and fourth switches 546 and 548, it is preferable to use a slide switch or the like which is OFF when the switch is present on the side of the front surface 562 of the extended section 554 and which is changed to ON when the switch is moved toward the rear surface 564. Similarly to the pressing switch, the slide switch is preferably formed to be changed to OFF by detaching the finger therefrom.

Needless to say, it is also preferable that the first and second switches 542 and 544 are the pressing switches and the third and fourth switches 546 and 548 are the slide switches or the like.

In the handle unit 512, a slip stopper (not shown) having a large number of protrusions may be formed at a position touched by the finger or palm of the hand H when the handle unit 512 is held, e.g., each of the side surfaces 566 and 568. At this time, for example, when the surfaces of the third and fourth switches 546 and 548 are smoothly formed, the third and fourth switches 546 and 548 can be found with the sense of the touch of the hand H without visually recognizing the third and fourth switches 546 and 548.

A second reference embodiment will now be described with reference to FIG. 23. This reference embodiment is a modification of the first reference embodiment, and like reference numerals denote the same members or members having the same functions as the members described in the first reference embodiment to omit a detailed description.

As shown in FIG. 23, differently from the first reference embodiment, this reference embodiment is an example where a third switch 546 is interposed between an origin O and a central portion of a surface of a second switch 544 on the side of a front surface 562 of an extended section 554. Also in this reference embodiment, the third switch 546 is closer to the central portion of the surface of the second switch 544 on the side of the front surface 562 of the extended section 554 than the origin O.

Furthermore, when a length La from the origin O to the third switch 546 is compared with a length Lb from the third switch 546 to the second switch 544, the lengths are preferably the same or the length from the origin O to the third switch 546 is preferably longer (La≥Lb). Here, (L2−La)/La is one or more.

Even when the third switch 546 is present at such a position, the switch is in a moving range of an index finger similarly to the first reference embodiment, and hence at the time of operating the second switch 544, the third switch 546 can be prevented from being operated. At the time of operating the third switch 546, the third switch 546 can easily be operated with a fingertip by bending the index finger.

A third reference embodiment will now be described with reference to FIG. 24. This reference embodiment is a modification of the first and second reference embodiments, and like reference numerals denote the same members or members having the same functions as the members described in the first and second reference embodiments to omit a detailed description.

As shown in FIG. 24, differently from the second reference embodiment, this reference embodiment is an example where a third switch 546 is interposed between an origin O and a central portion of a surface of a first switch 542 on the side of a front surface 562 of an extended section 554. Also in this reference embodiment, the third switch 546 is closer to the central portion of the surface of the first switch 542 on the side of the front surface 562 of the extended section 554 than the origin O.

Further, when a length La from the origin O to the third switch 546 is compared with a length Lb from the third switch 546 to the first switch 542, the lengths are preferably the same, or the length from the origin O to the third switch 546 is preferably longer (La≥Lb). Here, (L1−La)/La is one or more.

Even when the third switch 546 is present at such a position, the switch is in a moving range of an index finger similarly to the first and second reference embodiments, and hence at the time of operating the first switch 542, the third switch 546 can be prevented from being operated. At the time of operating the third switch 546, the third switch 546 can easily be operated with a fingertip by bending the index finger.

A fourth reference embodiment will now be described with reference to FIG. 25. This reference embodiment is a modification of the first to third reference embodiments, and like reference numerals denote the same members or members having the same functions as the members described in the first to third reference embodiments to omit a detailed description.

Figure 25:
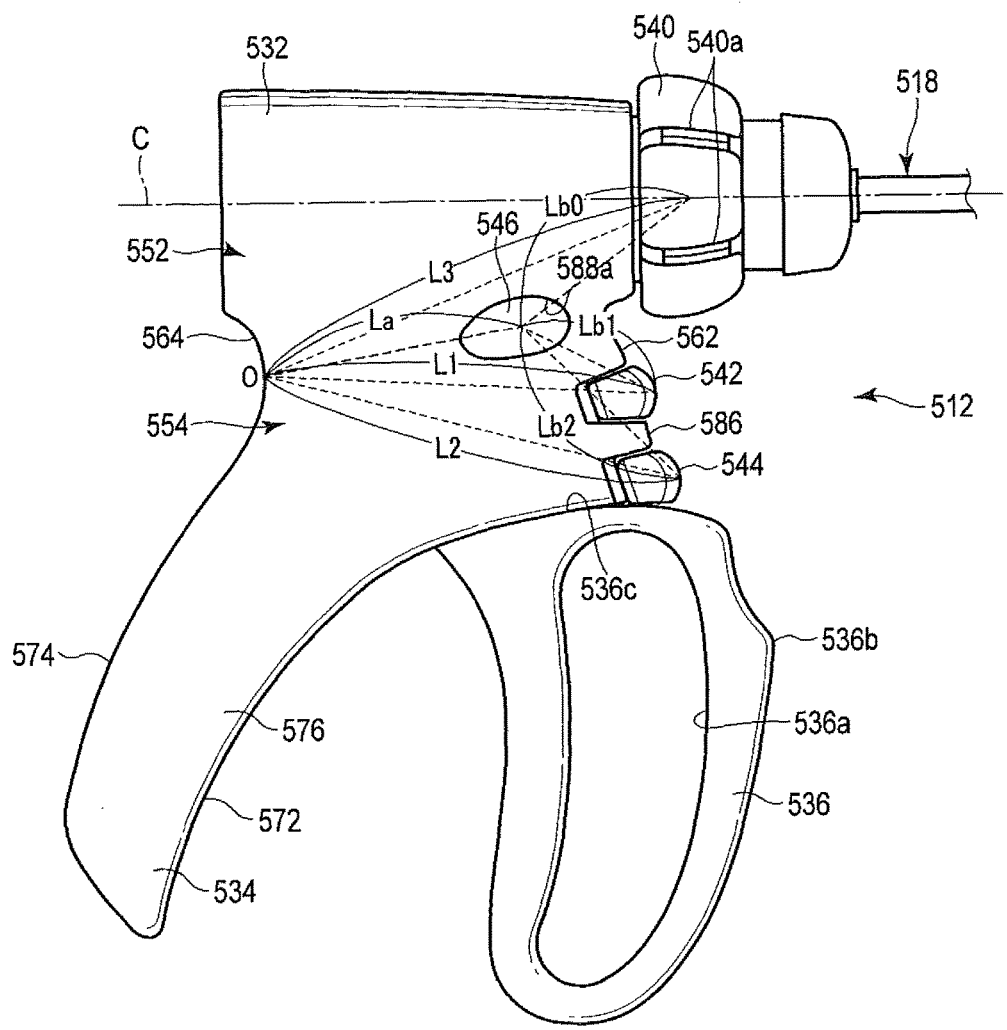
FIG. 25 is a schematic side view showing a right side surface of a handle unit of a surgical system according to a fourth reference embodiment.

As shown in FIG. 25, in this reference embodiment, differently from the first to third reference embodiments, a third switch 546 is not interposed between an origin O, and a central position between a distal end and a proximal end of a rotary knob 540 in a direction along a center axis C, and is not interposed between the origin O and a central portion of a surface of a second switch 544 on the side of a front surface 562 of an extended section 554. Furthermore, the third switch 546 of this reference embodiment is not interposed between the origin O and a central portion of a surface of a first switch 542 on the side of the front surface 562 of the extended section 554. Consequently, the third switch 546 is prevented from being wrongly operated in a state where a fingertip of an index finger is arranged on the rotary knob 540, the first switch 542 or the second switch 544.

Further, in this reference embodiment, the third switch 546 is present in a triangle formed by the origin O, the central position between the distal end and the proximal end of the rotary knob 540 in the direction along the center axis C, and the central portion of the surface of the second switch 544 on the side of the front surface 562 of the extended section 554. Consequently, the third switch 546 is present in a moving range of the index finger. Therefore, at the time of operating the rotary knob 540, the third switch 546 can be prevented from being operated when the first and second switches 542 and 544 are operated, and at the time of operating the third switch 546, the third switch 546 can easily be operated with the fingertip by bending the index finger.

It is to be noted that when a length La from the origin O to the third switch 546 is compared with a length Lb0 from the third switch 546 to the rotary knob 540, both the lengths are preferably the same, or the length from the origin O to the third switch 546 is preferably longer (La≥Lb0). Similarly, when the length La from the origin O to the third switch 546 is compared with a length Lb1 from the third switch to the first switch 542, both the lengths are preferably the same, or the length from the origin O to the third switch 546 is preferably longer (La≥Lb1). Further, the third switch 546 is present at a position closer to the front surface 562 of the extended section 554 than the origin O. Consequently, a moving amount of an index finger to the third switch 546 from the rotary knob 540 close to the front surface 562 of the extended section 554 (a bending/stretching amount of a joint) can be made smaller than that of a case where the third switch is disposed closer to the origin O (La<Lb0). Similarly, a moving amount of the index finger to the third switch 546 from the first switch 542 close to the front surface 562 of the extended section 554 (the bending/stretching amount of the joint) can be made smaller than that of the case where the third switch is disposed closer to the origin O (La<Lb1).

Furthermore, when the length La from the origin O to the third switch 546 is compared with a length Lb2 from the third switch 546 to the second switch 544, the lengths may be the same or different. However, the third switch 546 is operated with the index finger, and hence at the time of moving the index finger from the second switch 544 to the third switch 546 or in reverse, the bending/stretching amount of the joint of the index finger is preferably made smaller. Consequently, the third switch 546 is preferably present at a position closer to the side of the front surface 562 than to the side of a rear surface 564 of the extended section 554.

According to the abovementioned reference embodiments, the following items can be obtained.

(Item 1) A handle unit that allows an end effector to operate and substantially has the form of a pistol, comprising:

a body that has a front surface, a rear surface and a pair of side surfaces and in which a center axis is defined;

a fixed handle disposed continuously with the rear surface of the body;

a movable handle that is supported by the body on a side closer to the front surface of the body than the fixed handle, and movable closer to and away from the fixed handle;

a rotary knob that is disposed on the front surface of the body to be rotatable in a periaxial direction of the center axis, and turns the end effector in the periaxial direction of the center axis;

a first switch disposed in the front surface of the body;

a second switch disposed in the front surface of the body and disposed more away from the rotary knob than the first switch; and a third switch disposed in at least one of the pair of side surfaces of the body, wherein in a state where a web between a thumb and an index finger of a hand of a user is put on the rear surface of the body, the rotary knob and the first to third switches are present at respective positions reached by a finger sphere of a fingertip of the index finger of the same hand.

(Item 2) The handle unit according to Item 1, wherein when a position of the rear surface of the body at which the web between the thumb and the index finger of the hand of the user is put is an origin, the third switch is present in a region surrounded with the origin, the rotary knob and the second switch.

(Item 3) The handle unit according to Item 2,
wherein when a length from the origin to the third switch is La and a length from the origin to the rotary knob, the first switch or the second switch is La+Lb, La≥Lb.

(Item 4) The handle unit according to Item 1,
wherein in the state where the web between the thumb and the index finger of the user's hand is put on the rear surface of the body, the third switch is present at a position hidden with a portion between a finger sphere of a fingertip of the index finger and a base of the index finger when the rotary knob is supported with the finger sphere of the fingertip of the index finger of the user's hand, a position hidden with the portion between the finger sphere of the fingertip of the index finger and the base of the index finger when the first switch is supported with the finger sphere of the fingertip of the index finger of the user's hand, or a position hidden with the portion between the finger sphere of the fingertip of the index finger and the base of the index finger when the second switch is supported with the finger sphere of the fingertip of the index finger of the user's hand.

(Item 5) The handle unit according to Item 1,
wherein when a position of the rear surface of the body at which the web between the thumb and the index finger of the user's hand is put is an origin and a virtual parallel line passing the origin in parallel with the center axis is defined, the rotary knob and the third switch are present at positions inclined as much as about 20 degrees to the parallel line.

(Item 6) The handle unit according to Item 1,
wherein an outer surface of the third switch is present at a position of the same surface as the side surface of the body.

(Item 7) The handle unit according to Item 1,
wherein the side surface of the body has a receiving portion in which the third switch is received, and an annular concave portion formed continuously with the receiving portion, and
an outer surface of the third switch protrudes to the annular concave portion, and is present at a position of the same surface as the side surface of the body.

(Item 8) The handle unit according to Item 1,
wherein when a position of the rear surface of the body at which the web between the thumb and the index finger of the user's hand is put is an origin, a length from the origin to the second switch is longer than a length from the origin to the first switch.

(Item 9) The handle unit according to Item 1,
wherein one of the following functions is selected and set to each of the first to third switches:
i) allowing the end effector to treat a biological tissue with ultrasonic vibration, and outputting, from the end effector, energy to give a bipolar treatment;
ii) outputting, from the end effector, the energy to give the bipolar treatment;
iii) outputting, from the end effector, energy to give a monopolar treatment;
iv) outputting, from the end effector, energy to give a treatment with the ultrasonic vibration; and
v) outputting, from the end effector, energy to give the monopolar treatment and the treatment with the ultrasonic vibration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A handle unit for a surgical device that operates an end effector to give various kinds of treatments, the handle unit comprising:
a handle main body having a fixed member that is adapted to be supported by a user's hand to maintain a position of the end effector in a positioned state;
a support section that is located closer to a side of the end effector than a side of the fixed member and that is adapted to be supported by the same hand of the user, the support section being movable along a turning plane defined by moving closer to or away from the fixed member to operate the end effector;
a first coupling section that is coupled with the handle main body to operate the end effector by moving the support section along the turning plane;
an arm located between the first coupling section and the support section, the arm being movable around the first coupling section;
a second coupling section that is located within the arm, the second coupling section including a turning shaft that is orthogonal to a longitudinal axis of the support section, the second coupling section being configured to turn the support section about the turning shaft; and
a third coupling section that is located between the arm and the support section, the third coupling being configured to turn the support section about the longitudinal axis, the third coupling section including at least one of an elastic member or a buffer member configured to bias the third coupling section so that the support section is arranged in a neutral position.

2. The handle unit according to claim 1, further comprising:
a first arm that is close to the first coupling section; and
a second arm that is close to the support section,
wherein a turning amount of the second arm to the first arm is configured to be changed by the second coupling section and the third coupling section in a state where a position of the end effector is maintained.

3. The handle unit according to claim 1, wherein the third coupling section includes both the buffer member and the elastic member to maintain the support section in the neutral position, and to suppress sudden movement of the support section in a direction away from the neutral position.

4. The handle unit according to claim 3, wherein at least one of the buffer member and the elastic member is to maintain the support section in the neutral position while allowing the support section to be away from the neutral position.

5. The handle unit according to claim 3, wherein the second coupling section is configured to turn the support section in a periaxial direction orthogonal to the longitudinal axis.

6. The handle unit according to claim 1, wherein at least one of the second coupling section and the third coupling section includes a regulating body which regulates a turning range of the support section.

7. The handle unit according to claim 1, wherein the support section includes an annular portion on which a thumb of the hand of the user can be positioned.

8. The handle unit according to claim 7, wherein the fixed member includes an annular portion on which fingers other than the thumb can be positioned.

9. The handle unit according to claim 1, wherein the fixed member includes an annular portion on which a thumb of the hand of the user can be positioned.

10. The handle unit according to claim 9, wherein the support section includes an annular portion on which fingers other than the thumb can be positioned.

11. The handle unit according to claim 1, wherein
the handle main body has a center axis, and
the fixed member and the support section are present on one side of the center axis in the turning plane.

12. The handle unit according to claim 1, wherein
the handle main body has a center axis, and
the fixed member and the support section are present on sides mutually opposite to the center axis in the turning plane.

13. A surgical device comprising:
the handle unit according to claim 1; and
the end effector that is allowed to act on a biological tissue by an operation of the support section in the handle unit.

14. The surgical device according to claim 13, wherein the end effector is configured to be held at a fixed position irrespective of inclination of the handle unit by operating the support section in a direction away from the turning plane with the use of at least one of the first to third coupling sections when the handle unit is inclined by the user's operation.

15. The handle unit according to claim 1, wherein:
the turning shaft is arranged parallel to the turning plane; and
the second coupling section includes at least one of an elastic member or a buffer member configured to bias the second coupling section so that the support section is arranged in the neutral position.

* * * * *